US009879109B2

(12) United States Patent
Kojima et al.

(10) Patent No.: US 9,879,109 B2
(45) Date of Patent: Jan. 30, 2018

(54) RUBBER COMPOSITION FOR TIRES, TIRE MEMBER, AND PNEUMATIC TIRE

(71) Applicant: SUMITOMO RUBBER INDUSTRIES, LTD., Kobe-shi, Hyogo (JP)

(72) Inventors: Ryoji Kojima, Kobe (JP); Yuka Yokoyama, Kobe (JP); Masafumi Yoshino, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 0 days.

(21) Appl. No.: 14/420,575

(22) PCT Filed: Sep. 6, 2013

(86) PCT No.: PCT/JP2013/074015
§ 371 (c)(1),
(2) Date: Feb. 9, 2015

(87) PCT Pub. No.: WO2014/038647
PCT Pub. Date: Mar. 13, 2014

(65) Prior Publication Data
US 2015/0266988 A1    Sep. 24, 2015

(30) Foreign Application Priority Data
Sep. 7, 2012    (JP) .................. 2012-197502

(51) Int. Cl.
*C08F 236/10*    (2006.01)
*C07C 11/167*    (2006.01)
(Continued)

(52) U.S. Cl.
CPC .............. *C08F 236/10* (2013.01); *B60C 1/00* (2013.01); *B60C 1/0016* (2013.01);
(Continued)

(58) Field of Classification Search
CPC ........................ C08F 236/10; C07C 11/167
See application file for complete search history.

(56) References Cited

U.S. PATENT DOCUMENTS

2010/0216958 A1    8/2010 Peters et al.
2011/0172475 A1    7/2011 Peters et al.
(Continued)

FOREIGN PATENT DOCUMENTS

JP    2003-63206 A    3/2003
JP    2007-246712 A    9/2007
(Continued)

OTHER PUBLICATIONS

ChemNetBase (Styrene-butadiene rubber. Polymers: A Properties Database. 2016. 9 pages).*
(Continued)

*Primary Examiner* — Brieann R Johnston
(74) *Attorney, Agent, or Firm* — Birch, Stewart, Kolasch & Birch, LLP

(57) ABSTRACT

Provided are rubber compositions for tires capable of providing tire components and pneumatic tires that have the same level of fuel efficiency and wet grip performance (particularly, wet grip performance) as those of tire components and pneumatic tires containing conventional synthetic rubber, while satisfying the requirements for a sound material-cycle society. The present invention relates to rubber compositions for tires containing a biomass-derived rubber polymerized from an aromatic vinyl compound and a diene, the biomass-derived rubber having a pMC (percent modern carbon) measured in accordance with ASTM D 6866-10 of 1% or higher.

18 Claims, 2 Drawing Sheets

(51) Int. Cl.
*C08L 9/06* (2006.01)
*B60C 1/00* (2006.01)
*C12P 5/00* (2006.01)
*C12P 5/02* (2006.01)
*C08F 236/06* (2006.01)
*C08F 212/08* (2006.01)

(52) U.S. Cl.
CPC .......... *C07C 11/167* (2013.01); *C08F 236/06* (2013.01); *C08L 9/06* (2013.01); *C12P 5/005* (2013.01); *C12P 5/026* (2013.01); *C08F 212/08* (2013.01)

(56) References Cited

U.S. PATENT DOCUMENTS

| | | | |
|---|---|---|---|
| 2013/0005012 A1* | 1/2013 | Yu | C12N 9/88 435/166 |
| 2013/0090445 A1 | 4/2013 | Hattori et al. | |
| 2015/0274944 A1* | 10/2015 | Hogan | C08F 236/10 524/526 |

FOREIGN PATENT DOCUMENTS

| | | |
|---|---|---|
| JP | 2011-94011 A | 5/2011 |
| JP | 2011-99080 A | 5/2011 |
| JP | 2011-173510 A | 9/2011 |
| JP | 2012-52028 A | 3/2012 |
| JP | 2012-122016 A | 6/2012 |
| JP | 2012-153654 A | 8/2012 |
| JP | 2012-518658 A | 8/2012 |
| WO | WO 2009125037 A1 * 10/2009 ................ C12P 7/06 |
| WO | WO 2010/099201 A1 9/2010 |
| WO | WO 2011/085223 A1 7/2011 |
| WO | WO 2012/050931 A2 8/2012 |
| WO | WO 2012102290 A1 * 8/2012 ............. B01J 29/40 |
| WO | WO 2012178126 A1 * 12/2012 ............. C12N 9/88 |

OTHER PUBLICATIONS

Derwent Abstract of WO 2009125037 (Acc. No. 2009-P82911, 4 pages, Oct. 2009).*
International Search Report, issued in PCT/JP2013/074015, dated Oct. 29, 2013.
"Preparation Technology of New Food Raw Materials and the Use Thereof," Chemical Industry Press, Ed. Chen et al., p. 304, Feb. 29, 2014.
English translation of Second Office Action dated Sep. 20, 2016, in Chinese Patent Application No. 201380043562.8.

* cited by examiner

RUBBER COMPOSITION FOR TIRES, TIRE MEMBER, AND PNEUMATIC TIRE

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-05-29 5051-0350PUS1_ST25.txt" created on May 29, 2015 and is 2,392 bytes in size. The sequence listing contained in this .txt file is part of the specification and is hereby incorporated by reference herein in its entirety.

TECHNICAL FIELD

The present invention relates to rubber compositions for tires, and tire components and pneumatic tires containing the rubber compositions.

BACKGROUND ART

Currently marketed tires are made from raw materials derived from petroleum resources such that these raw materials account for half or more of the total weight of the tire. For example, common radial tires for passenger cars contain, based on the total weight of the tire, about 20% of synthetic rubber and about 20% of carbon black as well as aromatic oil and synthetic fibers. Thus, they contain at least 50% of petroleum-derived raw materials as a whole.

The recent emphasis on the environmental issues, however, has led to tighter $CO_2$ emission restrictions. Moreover, since the petroleum raw material is a limited resource and the amount of the material supplied is decreasing year by year, oil prices are expected to escalate in the future and thus the use of petroleum-derived raw materials has a limit.

Hence, the people's desire to construct a sound material-cycle society has recently become stronger. Accordingly, there is a need for a departure from fossil fuel dependence in the material field as well as in the energy field, and the use of biomass has been focused on.

For example, Patent Literature 1 discloses an environment-friendly tire technology to prepare for a future decrease in petroleum supply. In this technology, a tire is formed in which 75% by weight or more of the total weight of the tire is made from raw materials derived from resources other than petroleum, for example, by replacing synthetic rubber with natural rubber, carbon black with inorganic filler or bio filler, petroleum oil with vegetable oil or fat, and synthetic fibers with natural fibers.

However, unfortunately, natural rubber is inferior in fuel efficiency, wet grip performance, and processability (particularly, wet grip performance and processability) to synthetic rubber such as styrene-butadiene rubber (SBR).

CITATION LIST

Patent Literature

Patent Literature 1: JP 2003-63206 A

SUMMARY OF INVENTION

Technical Problem

It is an object of the present invention to solve the above problem and provide rubber compositions for tires capable of providing tire components and pneumatic tires that have the same level of fuel efficiency and wet grip performance (particularly, wet grip performance) as those of tire components and pneumatic tires containing conventional synthetic rubber, while satisfying the requirements for a sound material-cycle society.

Solution to Problem

The present invention relates to a rubber composition for tires, comprising a biomass-derived rubber polymerized from an aromatic vinyl compound and a diene, the biomass-derived rubber having a pMC (percent modern carbon) measured in accordance with ASTM D 6866-10 of 1% or higher.

The biomass-derived rubber preferably has a glass transition temperature (Tg) of −60° C. or higher.

The diene is preferably biomass-derived butadiene.

The aromatic vinyl compound is preferably biomass-derived styrene.

Preferably, the diene is biomass-derived butadiene, and the aromatic vinyl compound is biomass-derived styrene.

The butadiene is preferably obtained by a catalytic reaction from at least one biomass-derived ingredient selected from the group consisting of biomass-derived alkyl alcohols, allyl alcohols, alkenes, aldehydes, and unsaturated carboxylic acids.

The at least one of the alkyl alcohols is preferably at least one selected from the group consisting of ethanol, butanol, and butanediol.

The butanol is preferably produced by at least one selected from the group consisting of microorganisms, plants, animals, and tissue cultures thereof into which has been introduced at least one gene selected from the group consisting of mevalonate pathway-related genes, MEP/DOXP pathway-related genes, butyryl-CoA dehydrogenase encoding gene, butylaldehyde dehydrogenase encoding gene, and butanol dehydrogenase encoding gene.

The at least one of the allyl alcohols is preferably at least one of crotyl alcohol and 3-butene-2-ol.

The at least one of the alkenes is preferably at least one of butene and ethylene.

The ethylene is preferably converted from biomass by fermentation with the aid of at least one selected from the group consisting of microorganisms, plants, animals, and tissue cultures thereof.

The at least one of the microorganisms, plants, animals, and tissue cultures thereof for producing the ethylene preferably has an ACC synthase encoding gene which has been introduced, modified, or modified and introduced.

The at least one of the aldehydes is preferably acetaldehyde.

The at least one of the unsaturated carboxylic acids is preferably at least one of tiglic acid and angelic acid.

The butadiene is preferably directly produced from biomass by at least one selected from the group consisting of microorganisms, plants, animals, and tissue cultures thereof.

The butadiene is preferably converted from at least one selected from the group consisting of saccharides, hemiterpenes, and amino acids.

The at least one of the amino acids is preferably at least one selected from the group consisting of valine, leucine, isoleucine, and arginine.

The at least one of the hemiterpenes and amino acids is preferably converted to butadiene by at least one enzyme selected from the group consisting of HMG-CoA reductase, diphosphomevalonate decarboxylase, and amino acid decarboxylases.

The at least one of the microorganisms, plants, animals, and tissue cultures thereof for producing the butadiene preferably has at least one gene selected from the group consisting of HMG-CoA reductase encoding gene, diphosphomevalonate decarboxylase encoding gene, and amino acid decarboxylase encoding genes, which has been introduced, modified, or modified and introduced.

The styrene is preferably directly produced from biomass by at least one selected from the group consisting of microorganisms, plants, animals, and tissue cultures thereof.

The styrene is preferably converted from biomass-derived cinnamic acid.

The at least one of the plants is preferably at least one selected from the group consisting of plants of the families Hamamelidaceae, Styracaceae, Apocynaceae, Solanaceae, Daucus, and Theaceae.

The at least one of the microorganisms is preferably at least one selected from the group consisting of microorganisms of the genera *Fusarium, Penicillium, Pichia, Candida, Debaryomyces, Torulopsis, Saccharomyces, Bacillus, Escherichia, Streptomyces*, and *Pseudomonas*.

The at least one of the microorganisms is preferably not genetically modified.

The at least one of the microorganisms and plants is preferably engineered so as to highly express phenylalanine ammonia-lyase.

The at least one of the microorganisms and plants is preferably engineered so as to highly express cinnamate decarboxylase (phenylacrylate decarboxylase).

The at least one of the microorganisms and plants is preferably engineered so as to highly express phenolic acid decarboxylase.

The styrene is preferably obtained from biomass-derived cinnamic acid by plant metabolism.

The styrene is preferably obtained from biomass-derived cinnamic acid by microbial fermentation.

The styrene is preferably obtained from biomass-derived cinnamic acid by a catalytic reaction.

The butadiene is preferably a mixture of a plurality of biomass-derived butadienes of different origins.

The styrene is preferably a mixture of a plurality of biomass-derived styrenes of different origins.

The biomass-derived rubber preferably has a pMC of 100% or higher.

The biomass-derived rubber is preferably polymerized from a biomass-derived monomer component and a petroleum-derived monomer component.

The biomass-derived rubber is preferably polymerized from a biomass-derived monomer component or a combination of a biomass-derived monomer component and a petroleum-derived monomer component, in an appropriately chosen ratio depending on at least one of biomass resource supply situation, petroleum resource supply situation, and market needs.

Preferably, a saccharide content based on 100% by mass of the biomass is preferably 20% by mass or more.

Preferably, a combined content of amino acid and protein based on 100% by mass of the biomass is 10% by mass or more.

The present invention also relates to a rubber composition for tires, comprising a styrene-butadiene rubber polymerized from butadiene and styrene, at least part of the butadiene and styrene starting materials being obtained by a reaction or a series of reactions starting from biomass.

The present invention also relates to a method of producing a biomass-derived rubber polymerized from an aromatic vinyl compound and a diene, the biomass-derived rubber having a pMC (percent modern carbon) measured in accordance with ASTM D 6866-10 of 1% or higher, the method comprising polymerizing a biomass-derived monomer component or a combination of a biomass-derived monomer component and a petroleum-derived monomer component, in an appropriately chosen ratio depending on at least one of biomass resource supply situation, petroleum resource supply situation, and market needs.

The present invention also relates to a tire component, formed from the rubber composition.

The present invention also relates to a pneumatic tire, formed from the rubber composition.

Advantageous Effects of Invention

The present invention relates to rubber compositions for tires containing a biomass-derived rubber that is polymerized from an aromatic vinyl compound and a diene and has a pMC (percent modern carbon) measured in accordance with ASTM D 6866-10 of 1% or higher. Such compositions have the same level of fuel efficiency, wet grip performance, and processability (particularly, wet grip performance and processability) as when conventional synthetic rubber is used, while satisfying the requirements for a sound material-cycle society. Therefore, tire components and pneumatic tires containing such rubber compositions exhibit the same level of fuel efficiency and wet grip performance (particularly, wet grip performance) as those of tire components and pneumatic tires containing conventional synthetic rubber, while satisfying the requirements for a sound material-cycle society.

DESCRIPTION OF EMBODIMENTS

Figure 1:
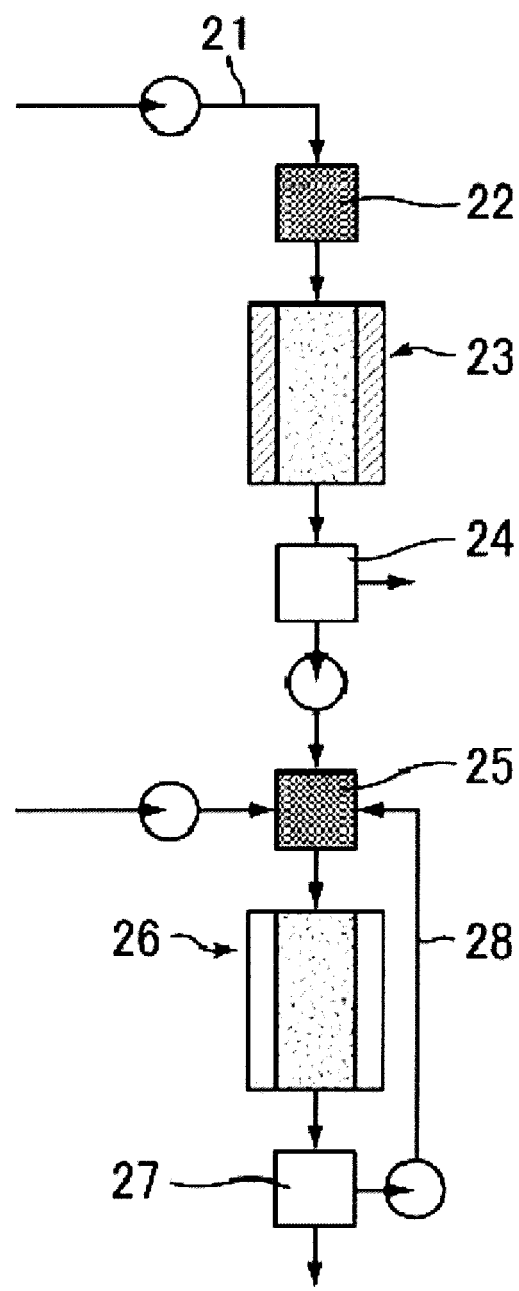
FIG. 1 is a schematic view simply illustrating a system used to produce butadiene.

The rubber compositions for tires of the present invention contain a biomass-derived rubber that is polymerized from an aromatic vinyl compound and a diene and has a pMC (percent modern carbon) measured in accordance with ASTM D 6866-10 of 1% or higher.

In the present invention, a biomass-derived rubber that is polymerized from an aromatic vinyl compound and a diene and has a pMC (percent modern carbon) measured in accordance with ASTM D 6866-10 of 1% or higher is used in the rubber component.

The pMC refers to a ratio of the $^{14}C$ content in a sample to that of a modern reference standard (modern standard reference). In the present invention, this value is used as an index of the biomass content in a compound (rubber). The following will describe what this value means.

One mole of carbon atoms ($6.02 \times 10^{23}$ carbon atoms) includes about $6.02 \times 10^{11}$ $^{14}C$ atoms (about one trillionth of the number of normal carbon atoms). $^{14}C$ is called a radioactive isotope and its half-life period is 5730 years and the number thereof regularly decreases. Decay of all the $^{14}C$ atoms requires 226,000 years. In other words, in the fossil fuels, such as coal, petroleum, and natural gas, which are considered to be at 226,000 years or longer after carbon dioxide and the like in the air were taken into and fixed in plants and the like, all the $^{14}C$ atoms which had been contained in these materials at the beginning of fixation are decayed. Thus, in the current 21st century, fossil fuels, such as coal, petroleum, and natural gas, contain no $^{14}C$ atoms. Accordingly, chemical materials prepared from such fossil fuel raw materials contain no $^{14}C$ atoms either.

Meanwhile, $^{14}C$ is unceasingly generated by nuclear reaction of cosmic rays in the atmosphere and this generation balances with the $^{14}C$ reduction due to radioactive decay. Thus, in the global atmosphere, the amount of $^{14}C$ is constant. Then, the $^{14}C$ content in materials derived from biomass resources which are being cycled in the current environment is about $1 \times 10^{-12}$ mol % of the total of C atoms as described above. Such a difference in amount permits calculation of the percentage of compounds derived from natural resources (compounds derived from biomass resources) (biomass content) in a compound (rubber).

The amount of $^{14}C$ is usually determined as follows. $^{13}C$ content ($^{13}C/^{12}C$) and $^{14}C$ content ($^{14}C/^{12}C$) are determined using tandem accelerator mass spectrometry. In the determination, the $^{14}C$ content in the natural carbon cycle at 1950 is used as a modern standard reference, that is, a standard $^{14}C$ content. The specific standard substance used is an oxalic acid standard offered by the National Institute of Standards and Technology (NIST), United States. The specific radioactivity of carbon (intensity of radioactivity of $^{14}C$ per gram of carbon) in the oxalic acid is corrected for carbon isotopic fractionation to a certain value for $^{13}C$, and then corrected for decay between 1950 AD to the measurement date. This corrected value is taken as a standard $^{14}C$ content (100%). The ratio between this value and the actual measurement value of a sample is defined as pMC in the present invention.

Accordingly, a rubber formed from 100% materials derived from biomass (natural materials) is expected to have about 110 pMC although there are some differences such as regional differences (currently, such materials often fail to exhibit a value of 100 in usual conditions). On the other hand, the $^{14}C$ content of chemical materials derived from fossil fuels, such as petroleum, is expected to be substantially 0 pMC (for example, 0.3 pMC). This value corresponds to a biomass content of 0% as mentioned above.

Thus, rubbers with a high pMC, in other words, rubbers with a high biomass content can be suitably used in rubber compositions for tires in view of environmental protection.

The biomass-derived rubber has a pMC (indicating a biomass content in the biomass-derived rubber) measured in accordance with ASTM D 6866-10 of 1% or higher, preferably 10% or higher, more preferably 50% or higher, and still more preferably 100% or higher. The upper limit is not particularly limited. Those having a higher pMC are preferred because they better satisfy the requirements for a sound material-cycle society. As described above, pMC may exceed 100% because it is by definition calculated as a ratio relative to a standard substance.

In the present invention, the pMC of the rubber (biomass-derived rubber) is measured in accordance with ASTM D 6866-10, and specifically can be measured by the method described in Examples.

As described in Examples, $^{14}C$ content analysis of rubber requires pretreatment of the rubber. Specifically, all the carbon atoms contained in rubber are oxidized and converted to carbon dioxide. Further, after the resulting carbon dioxide is separated from water and nitrogen, the carbon dioxide needs to be reduced and converted to graphite (solid carbon). Then, the resulting graphite is irradiated with cations such as $Cs^+$ so that carbon anions are generated. The carbon ions are accelerated using a tandem accelerator so that the anions are converted to cations by charge exchange reaction. The orbitals of $^{12}C^{3+}$, $^{13}C^{3+}$ and $^{14}C^{3+}$ are separated using a mass analysis electromagnet, and $^{14}C^{3+}$ can be measured with an electrostatic analyzer.

By using in rubber compositions for tires a biomass-derived rubber that is polymerized from an aromatic vinyl compound and a diene and has a pMC of not lower than a specific value, the present invention can solve the problem that cannot be solved by the prior art to provide tire components and pneumatic tires that have the same level of fuel efficiency and wet grip performance (particularly, wet grip performance) as those of tire components and pneumatic tires containing conventional synthetic rubber, while satisfying the requirements for a sound material-cycle society. In the present invention, the biomass is also referred to as biomass resources.

The biomass-derived rubber preferably has a glass transition temperature (Tg) of $-60°$ C. or higher. In spite of having a pMC of not lower than a specific value, the biomass-derived rubber having a Tg within the above range provides good fuel efficiency, wet grip performance, and processability (particularly, good wet grip performance and processability), which cannot be achieved by conventional 100% biomass-derived natural rubber. Thus, such a rubber can be used to provide tire components and pneumatic tires that have the same level of fuel efficiency and wet grip performance (particularly, wet grip performance) as those of tire components and pneumatic tires containing conventional synthetic rubber, while satisfying the requirements for a sound material-cycle society. The Tg is preferably $-55°$ C. or higher. If the Tg is lower than $-60°$ C., wet grip performance tends to be reduced. The Tg is also preferably $0°$ C. or lower, more preferably $-10°$ C. or lower, and still more preferably $-20°$ C. or lower. If the Tg is higher than $0°$ C., low-temperature properties tend to be reduced.

In the present invention, the Tg of the rubber (biomass-derived rubber) can be measured by the method described in Examples.

The Mw (weight average molecular weight) of the biomass-derived rubber is preferably $0.1 \times 10^4$ to $100 \times 10^4$, and more preferably $10 \times 10^4$ to $80 \times 10^4$ because then the effects of the present invention can be suitably achieved.

For the same reason, the Mw (weight average molecular weight)/Mn (number average molecular weight) ratio of the biomass-derived rubber is preferably 0.1 to 10, and more preferably 0.5 to 5.

The Mw and the Mn of the biomass-derived rubber can be measured by the method described in Examples.

The aromatic vinyl compound content (preferably the styrene content) in the biomass-derived rubber is preferably 5% by mass or more, more preferably 10% by mass or more, and still more preferably 20% by mass or more. If the aromatic vinyl compound content is less than 5% by mass, grip performance may be remarkably reduced. The aromatic vinyl compound content is preferably 60% by mass or less, more preferably 50% by mass or less, and still more preferably 40% by mass or less. If the aromatic vinyl compound content is more than 60% by mass, heat build-up tends to remarkably increase and fuel efficiency tends to deteriorate.

In the present invention, the aromatic vinyl compound content (preferably the styrene content) in the biomass-derived rubber is calculated by $H^1$-NMR measurement.

The biomass-derived rubber is polymerized from an aromatic vinyl compound and a diene. In the present invention, the rubber polymerized from an aromatic vinyl compound and a diene includes, in addition to rubbers polymerized from aromatic vinyl compounds and dienes by conventional methods, rubbers containing an aromatic vinyl compound and a diene as skeletal components, obtained by reactions using microorganisms, plants, animals, or tissue cultures thereof (hereinafter, also referred to as microorganisms or the like) or by enzymatic reactions.

Moreover, the biomass-derived rubber may be any one obtained by polymerizing an aromatic vinyl compound and a diene as monomers to satisfy the above-specified pMC. Specifically, in order for the biomass-derived rubber to satisfy the above-specified pMC, at least one of the aromatic vinyl compound and the diene needs to be derived from biomass (a biomass-derived monomer). Both the aromatic vinyl compound and the diene are preferably biomass-derived monomers because rubber with a higher pMC more suitably satisfies the requirements for a sound material-cycle society, as described above.

Furthermore, the biomass-derived monomer component may be used in combination with a petroleum-derived monomer component, as long as the above-specified pMC is satisfied. Specifically, the biomass-derived diene may be used in combination with a diene other than biomass-derived dienes (petroleum-derived diene). Similarly, the biomass-derived aromatic vinyl compound may be used in combination with an aromatic vinyl compound other than biomass-derived aromatic vinyl compounds (petroleum-derived aromatic vinyl compound).

Examples of the aromatic vinyl compounds (aromatic vinyl monomers) include styrene, vinylnaphthalene, and divinylnaphthalene. Styrene (particularly, biomass-derived styrene) is preferred among these in view of the physical properties (particularly, good grip performance) of the resulting polymer and availability for industrial applications. The styrene may be substituted.

The diene (diene monomer) is preferably a conjugated diene monomer, and examples thereof include butadiene (particularly, 1,3-butadiene), isoprene, 1,3-pentadiene (piperine), 2,3-dimethyl-1,3-butadiene, and 1,3-hexadiene. Butadiene (particularly, biomass-derived butadiene (1,3-butadiene)) is preferred among these in view of the physical properties of the resulting polymer and availability for industrial applications.

As long as the biomass-derived rubber satisfies the above pMC range, it may contain structural units derived from monomers other than aromatic vinyl compounds and dienes (copolymerizable monomers such as monoterpenes (e.g. myrcene)).

As for the ratio of the diene to the aromatic vinyl compound to be used, the diene to aromatic vinyl compound mass ratio is preferably 50/50 to 90/10, and more preferably 55/45 to 85/15. If the ratio is less than 50/50, the polymer rubber may be insoluble in hydrocarbon solvents and thus polymerization cannot be uniformly carried out. Conversely, if the ratio is more than 90/10, the polymer rubber may have a reduced strength.

As described above, the biomass-derived rubber is preferably a styrene-butadiene rubber polymerized from biomass-derived butadiene and styrene (biomass styrene-butadiene rubber (BSBR)) because such a rubber provides good fuel efficiency, wet grip performance, and processability (particularly, good wet grip performance and processability) while satisfying the requirements for a sound material-cycle society.

As long as the BSBR satisfies the above pMC range, it may contain structural units derived from monomers other than butadiene and styrene (copolymerizable monomers such as dienes other than butadiene (e.g., isoprene), aromatic vinyl compounds other than styrene (e.g., vinylnaphthalene), and monoterpenes (e.g. myrcene)). The butadiene and styrene may not be all derived from biomass. In other words, the biomass-derived butadiene may be used in combination with butadiene other than biomass-derived butadiene (petroleum-derived butadiene). Similarly, the biomass-derived styrene may be used in combination with styrene other than biomass-derived styrene (petroleum-derived styrene).

The biomass-derived monomer component content based on 100 mol % of the monomer component forming the biomass-derived rubber is not particularly limited, as long as the above pMC range is satisfied. The content is preferably 50 mol % or more, more preferably 70 mol % or more, still more preferably 80 mol % or more, particularly preferably 90 mol % or more, and most preferably 95 mol % or more and may be 100 mol %, because those having a higher pMC can more suitably satisfy the requirements for a sound material-cycle society, as described above.

Next, prior to describing methods of preparing biomass-derived rubbers from biomass, the biomass used in the present invention will be explained.

In the present invention, the biomass (biomass resources) means carbon-neutral organic resources of biological origin, and specifically includes: those converted to starch, cellulose or the like and stored; bodies of animals which eat plants to grow up; and products of processed plant or animal bodies, but excludes fossil resources.

The biomass resource may be edible or nonedible and is not particularly limited. In consideration of effective use of resources without competing with the demand as food, the biomass resource is preferably a nonedible raw material.

Specific examples of the biomass resources include cellulose crops (e.g. pulp, kenaf, straw, rice straw, wastepaper, and papermaking residues), wood, charcoal, compost, natural rubber, cotton, sugar cane, soy pulp, fats and oils (e.g. rapeseed oil, cottonseed oil, soybean oil, coconut oil, and castor oil), hydrocarbon crops (e.g. corn, tubers, wheat, rice, chaff, rice bran, old rice, cassava, and sago palm), bagasse, buckwheat, soybean, essential oils (e.g. pine root oil, orange oil, and eucalyptus oil), black liquor, kitchen garbage, waste vegetable oils, residues of aquatic products, livestock waste, food waste, algae, and drainage sludge.

The biomass resource may be obtained by treating any of the above resources (i.e., a biomass-derived material). The treatment may be carried out by known methods, such as, for example: biological treatments based on the activity of, for example, microorganisms, plants, animals, or tissue cultures thereof; chemical treatments using, for example, acids, alkalis, catalysts, thermal energy, or light energy; and physical treatments such as milling, compression, microwave treatment, and electromagnetic treatment.

The biomass resource may be refined or extracted from any of the aforementioned biomass resources and treated biomass resources (i.e., a biomass-derived material). For example, the biomass resource may be any of saccharides, proteins, amino acids, fatty acids, fatty acid esters, and others which are refined from biomass resources.

The saccharide may be any biomass-derived one, and examples thereof include sucrose, glucose, trehalose, fructose, lactose, galactose, xylose, allose, talose, gulose, altrose, mannose, idose, arabinose, apiose, maltose, cellulose, starch, and chitin.

The protein may be any biomass-derived compound that is formed by linking amino acids (preferably L-amino acids), and include oligopeptides such as dipeptides.

The amino acid may be any biomass-derived organic compound containing both amino and carboxyl functional groups. Examples thereof include valine, leucine, isoleucine, arginine, lysine, asparagine, glutamine, and phenylalanine. Preferred among these are valine, leucine, isoleucine, arginine, and phenylalanine. The amino acid may be an L-amino acid or a D-amino acid, but it is preferably an L-amino acid because it is present in a large amount in nature and can be easily used as a biomass resource.

The fatty acid may be any biomass-derived one, and examples thereof include butyric acid, oleic acid, linoleic acid, palmitic acid, and stearic acid.

The fatty acid ester may be any biomass-derived one, and examples thereof include animal-derived fats, vegetable oils, and modified biomass-derived fats and oils.

The biomass resource may contain various materials and impurities. For efficient conversion, however, the saccharide content based on 100% by mass of the biomass is preferably 20% by mass or more, more preferably 30% by mass or more, and still more preferably 50% by mass or more. In another embodiment, for efficient conversion, the combined content of amino acid and protein based on 100% by mass of the biomass is preferably 10% by mass or more, more preferably 20% by mass or more, and still more preferably 30% by mass or more. In yet another embodiment, for efficient conversion, the combined content of fatty acid and fatty acid ester based on 100% by mass of the biomass is preferably 10% by mass or more.

The following will describe methods of preparing biomass-derived rubbers from biomass. As described above, since the biomass-derived rubber is preferably a styrene-butadiene rubber polymerized from biomass-derived butadiene and styrene (biomass styrene-butadiene rubber (BSBR)), a typical example in which the biomass-derived rubber is BSBR is specifically described below. As described above, in the present invention, the BSBR includes, in addition to BSBRs polymerized from biomass-derived butadiene and styrene by conventional methods, BSBRs obtained by reactions using microorganisms or the like or by enzymatic reactions.

First, methods of preparing butadiene from biomass resources are described, but the method of preparing butadiene is not limited to the methods described below.

Butadiene may be prepared from biomass resources by any of various methods. Examples thereof include: biological treatments in which butadiene is directly prepared from a biomass resource using at least one selected from the group consisting of microorganisms, plants, animals, and tissue cultures thereof; methods of performing the aforementioned chemical treatments on biomass resources to prepare butadiene; methods of performing the aforementioned physical treatments on biomass resources to prepare butadiene; methods of converting biomass resources to butadiene by in-vitro enzymatic reactions or the like; and any combination of these methods. The at least one of the microorganisms, plants, and animals which convert biomass resources to butadiene may or may not be genetically engineered.

The direct conversion of butadiene from biomass resources using microorganisms or the like may be accomplished by any method, and can be carried out using an in-vivo pathway where an amino acid is converted to an alkyl alcohol and/or a hemiterpene.

The amino acid is preferably valine, leucine, isoleucine, or arginine. Moreover, the hemiterpene is preferably tiglic acid and/or angelic acid.

Preferably, butadiene may be prepared from an amino acid and/or a hemiterpene using a microorganism, plant, animal, or tissue culture thereof, in which a gene encoding an enzyme having a decarboxylase activity and/or a gene encoding an enzyme having a reductase activity has been introduced and/or modified.

Examples of the enzymes having a decarboxylase activity include diphosphomevalonate decarboxylase (EC 4.1.1.33) and various amino acid decarboxylases. Examples of the enzymes having a reductase activity include HMG-CoA reductase and 12-oxophytodienoate reductase (EC 1.3.1.42).

Preferred methods of producing butadiene by fermentation through an amino acid-mediated in-vivo reaction include a method of producing butadiene by reacting any of various decarboxylases with tiglic acid and/or angelic acid, which can be synthesized in vivo from isoleucine through natural metabolic pathways of microorganisms or the like. Alternatively, butadiene may be prepared by decarboxylase reactions using various fatty acid derivatives produced during amino acid metabolism.

The amino acid required for preparing butadiene may directly be added to a medium. It is preferred to use a biosynthetic amino acid synthesized in vivo by fermentation of a ground plant, a livestock waste or the like. In this case, butadiene rubber is converted from a saccharide and/or a protein.

Usual methods of producing alcohols or alkenes by fermentation mainly utilize saccharides as biomass resources; in contrast, the above production methods have great potential to effectively utilize biomass resources mainly containing amino acids and proteins and thus are useful.

Other preferred methods of preparing butadiene from biomass resources include methods in which an intermediate capable of being used to synthesize butadiene is prepared from a biomass resource using at least one selected from the group consisting of microorganisms, plants, animals, and tissue cultures thereof, and the intermediate is then subjected to, for example, any of the aforementioned chemical treatments, such as catalytic reactions, the aforementioned physical treatments, the aforementioned in-vitro enzymatic reactions, and combinations of these methods to prepare butadiene (dienes such as butadiene).

Examples of the intermediates capable of being used to synthesize butadiene include alkyl alcohols, allyl alcohols, alkenes, aldehydes, and unsaturated carboxylic acids.

The alkyl alcohol may be any biomass-derived one, and is preferably ethanol, butanol, or butanediol, and more preferably butanol or butanediol. The butanol may be 1-butanol or 2-butanol, or a mixture thereof.

Various methods are known to produce from biomass resources ethanol (biomass resource-derived ethanol is also referred to as bioethanol) or butanol (biomass resource-derived butanol is also referred to as biobutanol) by fermentation with the aid of microorganisms or the like. Typical examples thereof include a method of producing bioethanol from a biomass resource (e.g. sugar cane or glucose) by the fermentation of ethanol by yeast, and a method of producing biobutanol from a biomass resource (e.g. glucose) by the fermentation of acetone and butanol (ABE fermentation) by fermentative microbes. In the ABE fermentation method, a solvent mixture of butanol, acetone, and others is obtained, and this mixture can then be distilled to provide biobutanol.

Also, butanol may directly be prepared from bioethanol by a catalytic reaction, or may be prepared via acetaldehyde.

The ABE fermentation microorganism may be any microorganism capable of ABE fermentation. Examples thereof include microorganisms of the genera *Escherichia, Zymomonas, Candida, Saccharomyces, Pichia, Streptomyces, Bacillus, Lactobacillus, Corynebacterium, Clostridium,* and *Saccharomyces*. Such a microorganism may be any type of strain, including wild-type and mutant strains, and recombinant strains induced by genetically engineering techniques, such as cell fusion or gene manipulation. Preferred among these microorganisms are microorganisms of the genus *Clostridium*, and more preferred are *Clostridium acetobutylicum, Clostridium beijerinckii, Clostridium saccharobutylicum,* and *Clostridium saccharoperbutylacetonicum*.

For example, a preferred method of producing biobutanol is to produce butanol by fermentation with the aid of at least one selected from the group consisting of microorganisms, plants, animals, and tissue cultures thereof into which has been introduced at least one gene selected from the group consisting of mevalonate pathway-related genes, MEP/DOXP pathway-related genes, butyryl-CoA dehydrogenase encoding gene, butylaldehyde dehydrogenase encoding gene, and butanol dehydrogenase encoding gene (for example, see JP 2010-508017 T).

The ethanol and butanol produced by fermentation of biomass resources are also commercially available as bioethanol and biobutanol (e.g., biobutanol of Du Pont), respectively.

Moreover, various fermentative methods of directly preparing butanediol as material for bioplastics have been developed (for example, Syu M. J., Appl. Microbial Biotechnol. 55:10-18 (2001); Qin et al., Chinese J. Chem. Eng. 14 (1):132-136 (2006); JP 2011-522563 T; JP S62-285779 A; and JP 2010-115116 A), and such butanediol can easily be used as bio-derived butanediol. The butanediol may also be prepared by conversion of biomass-derived succinic acid, fumaric acid, furfural, or the like.

The butanediol fermentation microorganism may be any microorganism capable of butanediol fermentation. Examples thereof include microorganisms of the genera *Escherichia, Zymomonas, Candida, Saccharomyces, Pichia, Streptomyces, Bacillus, Lactobacillus, Corynebacterium, Clostridium, Klebsiella,* and *Saccharomyces*. Such a microorganism may be any type of strain, including wild-type and mutant strains, and recombinant strains induced by genetically engineering techniques, such as cell fusion or gene manipulation.

Preferred among these microorganisms are microorganisms of the genera *Bacillus, Clostridium,* and *Klebsiella*, and more preferred are *Clostridimn autoethanogenum, Bacillus polymyxa, Bacillus subtilis, Bacillus pumilus, Bacillus macerans, Bacillus licheniformis, Bacillus megaterium,* and *Klebsiella pneumoniae*.

The alkyl alcohol may be converted to butadiene for example by the aforementioned biological treatments, such as fermentation, the aforementioned chemical treatments, such as catalytic reactions, the aforementioned physical treatments, the aforementioned in-vitro enzymatic reactions, or any combination of these methods.

For direct conversion of the alkyl alcohol to butadiene, for example, a method is known in which ethanol and/or butanol is converted to butadiene using a dehydration or dehydrogenation catalyst, such as hydroxyapatite, $Ta/SiO_2$, alumina, or zeolite.

The allyl alcohol may be any biomass-derived one. For easy conversion to butadiene, crotyl alcohol and 3-buten-2-ol are preferred.

The crotyl alcohol and 3-buten-2-ol may directly be produced from biomass resources by fermentation with the aid of microorganisms or the like, or may be prepared by reducing biomass-derived crotonic acid or its derivatives. Also, the crotyl alcohol may be prepared from biomass-derived butanediol using a catalyst, such as zeolite, alumina, or cerium oxide (for example, see JP 2004-306011 A).

For conversion of the allyl alcohol to butadiene, mention may be made of a method of converting crotyl alcohol to butadiene by dehydration using a commonly known catalytic reduction catalyst, such as zeolite or alumina.

The alkene may be any biomass-derived one, and preferred are ethylene and butene (also referred to as butylene), with ethylene being more preferred.

The biomass-derived ethylene and butene may be prepared, for example, by a method of converting bioethanol to ethylene using a dehydration catalyst (e.g. alumina and zeolite) or by high-temperature treatment, and a method of converting biobutanol to butene using a dehydration catalyst (e.g. alumina and zeolite) or by high-temperature treatment, respectively.

These alkenes (ethylene and butene) can also directly be produced from biomass resources by fermentation with the aid of at least one selected from the group consisting of microorganisms, plants, animals, and tissue cultures thereof.

In preferred, but nonlimiting, embodiments, in view of productivity, the at least one of the ethylene fermentation microorganisms, plants, animals, and tissue cultures thereof has a gene encoding an enzyme having an ACC synthase (ethylene synthase) activity that has been introduced and/or modified.

In preferred, but nonlimiting, embodiments, the at least one of the butene fermentation microorganisms, plants, animals, and tissue cultures thereof has a gene encoding an enzyme having a diphosphomevalonate decarboxylase (EC 4.1.1.33) activity that has been introduced and/or modified (for example, see JP 2011-526489 T).

For conversion of the alkene to butadiene, mention may be made, for example, of: a method of converting butene to butadiene using alumina, zeolite, or the like; and a method of partially converting ethylene to acetaldehyde using an oxidation catalyst such as palladium chloride or palladium acetate, and then subjecting the acetaldehyde to a dehydration reaction with the remaining ethylene using a dehydration catalyst such as alumina or zeolite to prepare butadiene.

The aldehyde may be any biomass-derived one, and is preferably acetaldehyde.

The acetaldehyde may directly be produced from biomass resources by fermentation with the aid of microorganisms or the like, or may be converted from biomass-derived ethylene using an oxidation catalyst such as palladium chloride.

For conversion of the aldehyde to butadiene, mention may be made of a method including a dehydration reaction with ethylene, for example.

The unsaturated carboxylic acid may be any biomass-derived one, and tiglic acid and angelic acid are preferred.

The tiglic acid and angelic acid may directly be produced from biomass resources by fermentation with the aid of microorganisms or the like. Specifically, tiglic acid and angelic acid can be synthesized in vivo from isoleucine through natural metabolic pathways of microorganisms or the like. Alternatively, they may be refined from croton oil or the like.

For conversion of the unsaturated carboxylic acid to butadiene, mention may be made, for example, of: a method of reacting any of various decarboxylases with tiglic acid and/or angelic acid to cause conversion; and a method including reaction with a metal catalyst (e.g. palladium), zeolite, alumina or the like to cause conversion.

Butadiene can be obtained from biomass resources by the above-described methods or the like.

The following will describe methods of preparing styrene from biomass resources, but the method of preparing styrene is not limited to the methods described below.

Styrene may be prepared from biomass resources by any of various methods. Examples thereof include: biological treatments in which styrene is directly prepared from biomass resources using at least one selected from the group consisting of microorganisms, plants, animals, and tissue cultures thereof (particularly, microorganisms, plants, and tissue cultures thereof); methods of performing the aforementioned chemical treatments on biomass resources to prepare styrene; methods of performing the aforementioned physical treatments on biomass resources to prepare styrene; methods of converting biomass resources to styrene by in-vitro enzymatic reactions or the like; and any combination of these methods. Preferred among these are biological treatments. In such methods, saccharides, which are used as carbon source in a medium, are used as main biomass resources. The at least one of the microorganisms, plants, and animals which convert biomass resources to styrene may or may not be genetically engineered.

The direct conversion (biological treatment) of styrene from biomass resources using microorganisms or the like may be accomplished by any method, and can be carried out using an in-vivo pathway where styrene is biosynthesized from phenylalanine via cinnamic acid.

Phenylalanine is a material biosynthesized through a shikimic acid pathway present in most of microorganisms or plants. An in-vivo pathway where styrene is biosynthesized from such phenylalanine via cinnamic acid is known. Thus, styrene can directly be produced from biomass resources through such an in-vivo pathway of microorganisms or the like using at least one selected from the group consisting of microorganisms, plants, animals, and tissue cultures thereof (particularly, microorganisms, plants, and tissue cultures thereof).

For efficient production of styrene, the at least one of the microorganisms, plants, animals, and tissue cultures thereof (particularly, microorganisms, plants, and tissue cultures thereof) is preferably engineered so as to highly express phenylalanine ammonia-lyase, cinnamate decarboxylase (phenylacrylate decarboxylase), and/or phenolic acid decarboxylase (particularly, ferulic acid decarboxylase).

Similarly, for efficient production of styrene, the at least one of the microorganisms, plants, animals, and tissue cultures thereof (particularly, microorganisms, plants, and tissue cultures thereof) is preferably modified so as to boost the production of (or excessively produce) phenylalanine, which is considered as a substrate in the styrene biosynthesis pathway.

Specifically, the at least one of the microorganisms, plants, animals, and tissue cultures thereof (particularly, microorganisms, plants, and tissue cultures thereof) is preferably engineered so as to highly express a shikimic acid pathway-related enzyme and/or a feedback inhibition enzyme.

More specifically, it is preferred that the at least one of the microorganisms, plants, animals, and tissue cultures thereof (particularly, microorganisms, plants, and tissue cultures thereof) highly express a shikimic acid pathway-related enzyme, express an L-phenylalanine biosynthesis pathway-related enzyme on which feedback inhibition by L-phenylalanine is cancelled, and/or highly express an enzyme on which feedback inhibition is cancelled.

Examples of the shikimic acid pathway-related enzymes include, but are not limited to, arogenate dehydratase, prephenate aminotransferase, prephenate dehydratase, and chorismate mutase.

For efficient production of styrene, it is preferred to add phenylalanine and/or cinnamic acid (preferably biomass-derived phenylalanine and/or cinnamic acid) to a medium for culturing microorganisms or the like (including the soil for cultivating plants). Styrene can be efficiently produced by adding the compound (s), which is located on the upstream side of the in-vivo pathway for biosynthesizing styrene. The phenylalanine and cinnamic acid to be added may be prepared by culturing microorganisms or the like.

The microorganism capable of directly converting a biomass resource to styrene is not particularly limited, and examples thereof include microorganisms of the genera *Fusarium, Penicillium, Pichia, Candida, Debaryomyces, Torulopsis, Saccharomyces, Bacillus, Escherichia, Streptomyces*, and *Pseudomonas*. Such a microorganism may be any type of strain, including wild-type and mutant strains, and recombinant strains induced by genetically engineering techniques, such as cell fusion or gene manipulation.

The microorganism of the genus *Fusarium* is not particularly limited and, for example, *F. oxysporum, F. roseum, F. aquasductuum, F. fujikuroi, F. solani, F. graminearum, F. asiaticum*, and *F. culmorum* are preferred in view of styrene conversion efficiency. More preferred is *F. oxysporum*.

The microorganism of the genus *Penicillium* is not particularly limited and, for example, *P.citrinum, P.oxalicum, P.glabrum, P.chrysogenum, P.digitatum, P.camemberti, P.islandicum, P.verrucosum, P.cyclopium, P.commune, P.citroviride, P.rugulosum, P.italicum, P.expansum, P.marneffei, P.griseofluvum, P.galaucum, P.roqueforti, P.camamberti, P.natatum*, and *P.gladioli* are preferred in view of styrene conversion efficiency. More preferred are *P.citrinum, P.oxalicum*, and *P.camamberti*, with *P.citrinum* being still more preferred.

The microorganism of the genus *Pichia* is not particularly limited and, for example, *Pichia carsonii, Pichia anomala, Pichia pastoris, Pichia farinosa, Pichia membranifaciens*, and *Pichia angusta* are preferred in view of styrene conversion efficiency. More preferred is *Pichia carsonii*.

The microorganism of the genus *Candida* is not particularly limited and, for example, *C.famata, C.etchellsii, C.versatilis*, and *C.stellata* are preferred in view of styrene conversion efficiency. More preferred is *C.famata*.

The microorganism of the genus *Debaryomyces* is not particularly limited and, for example, *Debaryomyces hansenii* is preferred in view of styrene conversion efficiency.

The microorganism of the genus *Torulopsis* is not particularly limited.

The microorganism of the genus *Saccharomyces* is not particularly limited and, for example, *S.cerevisiae, S.bayanus*, and *S.boulardii* are preferred in view of styrene conversion efficiency.

The microorganism of the genus *Bacillus* is not particularly limited and, for example, *B.subtilis, B.thuringiensis, B.coagulans, B.licheniformis*, and *B.megaterium* are preferred in view of styrene conversion efficiency. More preferred is *B.subtilis*.

The microorganism of the genus *Escherichia* is not particularly limited and, for example, *E.albertii, E.blattae,*

*E.coli, E.fergusonii, E.hermannii*, and *E.vulneris* are preferred in view of styrene conversion efficiency. More preferred is *E.coli*.

The microorganism of the genus *Streptomyces* is not particularly limited and, for example, *S.griseus, S.kanamyceticus, S.peucetius, S.galilaeus, S.parvulus, S.antibioticus, S.lividans*, and *S.maritimus* are preferred in view of styrene conversion efficiency.

The microorganism of the genus *Pseudomonas* is not particularly limited and, for example, *P.aeruginosa, P.syringae* pv. *Japonica, P.meliae*, and *P.putida* are preferred in view of styrene conversion efficiency. More preferred are *P.putida, P.putida* IH-2000, and *P.putida* S12, with *P.putida* IH-2000 or *P.putida* S12 being still more preferred.

The microorganism capable of directly converting a biomass resource to styrene is preferably a microorganism of the genus *Penicillium* or *Escherichia*, and more preferably *P.citrinum* or transformed *E.coli*.

The plant capable of directly converting a biomass resource to styrene is not particularly limited, and examples thereof include plants of the families Hamamelidaceae, Styracaceae, Apocynaceae, Solanaceae, Daucus, and Theaceae. Such a plant may be any type of strain, including wild-type and mutant strains, and recombinant strains induced by genetically engineering techniques, such as cell fusion or gene manipulation.

The plant (tree) of the family Hamamelidaceae is not particularly limited, and plants (trees) of the genus *Liquidambar* are preferred in view of styrene production efficiency. More preferred among these are *Liquidambar formosana, Liquidambar styraciflua*, and *Liquidambar orientalis*, and still more preferred are *Liquidambar styraciflua* and *Liquidambar orientalis*, with *Liquidambar styraciflua* being particularly preferred.

The plant (tree) of the family Styracaceae is not particularly limited, and plants (trees) of the genus *Styrax* are preferred in view of styrene production efficiency. More preferred among these are *Styrax officinalis, Styrax japonica*, and *Styrax benzoin Dryander*, with *Styrax japonica* being still more preferred.

The plant of the family Apocynaceae is not particularly limited, and plants of the genera *Catharanthus, Nerium, Vinca, Allamanda*, and *Ecdysanthera* are preferred in view of styrene production efficiency. More preferred are plants of the genus *Catharanthus* (particularly, *Catharanthus roseus*).

The plant of the family Solanaceae is not particularly limited, and plants of the genus *Nicotiana* are preferred in view of styrene production efficiency. More preferred are *N.tabacum* and *N.rustica*.

The plant of the family Daucus is not particularly limited, and plants of the genus Daucus are preferred in view of styrene production efficiency.

The plant of the family Theaceae is not particularly limited, and plants of the genera *Camellia, Cleyera*, and *Ternstroemia* are preferred in view of styrene production efficiency.

The plant capable of directly converting a biomass resource to styrene is preferably a plant of the family Hamamelidaceae, Styracaceae, or Apocynaceae, more preferably a plant of the genus *Liquidambar, Styrax*, or *Catharanthus*, still more preferably *Liquidambar styraciflua, Liquidambar orientalis, Styrax japonica*, or *Catharanthus roseus*, and particularly preferably *Liquidambar styraciflua, Styrax japonica*, or *Catharanthus roseus*.

In the case where the plant is a tree, styrene may be obtained from the tree by any method, and is preferably obtained by purifying a resin (sap) exuded from a scratched tree trunk, in view of efficiency. Alternatively, styrene may be obtained by grinding the tree bark, trunk, branch, root, or leaf and subjecting it to, for example, extraction with an appropriate solvent, heating and/or ultrasonic irradiation to obtain volatile components, followed by purification.

In the case where the plant is not a tree, although styrene is difficult to obtain as a resin, styrene may be obtained by grinding the plant tissue (e.g. stem, leaf, root, flower) and subjecting it to, for example, extraction with an appropriate solvent, heating and/or ultrasonic irradiation to obtain volatile components, followed by purification.

Alternatively, styrene may be obtained by culturing the plants tissue, subjecting the cultured tissue to, for example, extraction with an appropriate solvent, heating and/or ultrasonic irradiation to obtain volatile components.

The plant tissue to be cultured is not particularly limited, and is preferably a callus induced from a plant tissue section because then styrene can be efficiently obtained. That is, it is preferred to induce a callus from a plant tissue section and then culture the induced callus.

The callus may be induced by any method. For example, the callus is induced by culturing a plant tissue section (e.g. bud, leaf, or stem) in a medium containing a plant growth hormone (s) (e.g. an auxin plant hormone (e.g. dichlorophenoxyacetic acid) and/or a cytokinin plant hormone (e.g. benzyl adenine)).

Other preferred methods of preparing styrene from biomass resources include methods in which an intermediate (particularly, phenylalanine and/or cinnamic acid) capable of being used to synthesize styrene is prepared from a biomass resource using at least one selected from the group consisting of microorganisms, plants, animals, and tissue cultures thereof (particularly, microorganisms, plants, and tissue cultures thereof), and the prepared intermediate (particularly, phenylalanine and/or cinnamic acid) is then subjected to, for example, any of the aforementioned biological treatments, the aforementioned chemical treatments, such as catalytic reactions, the aforementioned physical treatments, the aforementioned in-vitro enzymatic reactions, and combinations of these methods to prepare styrene. Preferred among these are methods in which the prepared intermediate (particularly, phenylalanine and/or cinnamic acid) is subjected to any of the aforementioned biological treatments.

The at least one of the microorganisms, plants, and animals which convert the intermediate to styrene may or may not be genetically engineered.

The method of preparing styrene by subjecting the prepared intermediate (particularly, phenylalanine and/or cinnamic acid) to the biological treatment may be accomplished, for example, by adding phenylalanine and/or cinnamic acid to the medium for culturing microorganisms or the like (including the soil for cultivating plants), and culturing the microorganisms or the like in the medium, as described above. Thus, styrene can be biosynthesized from the added phenylalanine and/or cinnamic acid by the microorganisms or the like.

As the method of preparing styrene by subjecting the prepared intermediate, phenylalanine, to the chemical treatment such as a catalytic reaction, mention may be made of, for example, a method in which the phenylalanine is reacted with ammonia lyase, such as phenylalanine ammonia-lyase, and thereby converted to cinnamic acid, which is then decarboxylated using a decarboxylase, transition metal catalyst, zeolite or the like to prepare styrene; and a method in which the phenylalanine is directly treated with zeolite, alumina or the like at high temperatures to prepare styrene.

As the method of preparing styrene by subjecting the prepared intermediate, cinnamic acid, to the chemical treatment such as a catalytic reaction, mention may be made, for example, of a method in which the cinnamic acid is reacted with a metal catalyst containing a transition metal or the like, zeolite, alumina or the like at high temperatures for decarboxylation to prepare styrene.

Styrene can be obtained from biomass resources by the above-described methods or the like.

The method of polymerizing a styrene-butadiene rubber (biomass styrene-butadiene rubber (BSBR)) from the butadiene and styrene obtained from biomass resources by any of the aforementioned methods may be similar to, but not limited to, any of the methods of polymerizing styrene-butadiene rubber from petroleum-derived butadiene and styrene as known to the skilled person.

In view of ease of availability, the performance of the resulting BSBR, and the like, the butadiene obtained from biomass resources may suitably be a butadiene derived from an alkyl alcohol (preferably ethanol or butanol (more preferably butanol)), a butadiene derived from an alkene (preferably ethylene), or a butadiene derived from an unsaturated carboxylic acid (preferably tiglic acid). It may also suitably be a combination of these butadienes.

In view of ease of availability and the performance of the resulting BSBR, the styrene obtained from biomass resources may suitably be a styrene produced by a plant (preferably a plant of the family Hamamelidaceae, Styracaceae, or Apocynaceae, more preferably a plant of the genus *Liquidambar, Styrax*, or *Catharanthus*, and still more preferably *Liquidambar styraciflua, Styrax japonica*, or *Catharanthus roseus*) or a styrene produced by a microorganism (preferably a microorganism of the genus *Penicillium* or *Escherichia*, and more preferably *P.citrinum* or transformed *E.coli*). It may also suitably be a combination of these styrenes.

The molecular weight, branching, and microstructure of the resulting BSBR can appropriately be chosen by varying the polymerization conditions in accordance with conventionally known methods, depending on the desired tire performance.

Currently, there are some plans to develop biomass industrial complexes mainly for bioethanol, bioethylene, and the like. Bioethanol and bioethylene are produced mainly from saccharides and/or celluloses as biomass resources, and the effective use of other biomass resources, such as proteins, lipids, and amino acids, has not been achieved. In addition, the use of saccharides leads to competition with the demand as food and the overharvesting of celluloses leads to deforestation; therefore, a situation that is not necessarily environment-friendly may be caused.

Thus, the biomass-derived monomer component is preferably used in the form of a combination of a plurality of biomass-derived monomers, or a combination of the biomass-derived monomer component and a petroleum-derived monomer component, or a combination of these monomer components in an optimally adjusted ratio, depending on the comprehensive environmental needs, including the situation of supplying various biomass resources, the petroleum resource supply situation, and market needs (e.g. the trend of competition with the demand for biomass resources as food). This allows effective use of a wide variety of biomass resources such as saccharides, proteins, and lipids, without dependence on a single biomass resource, thus resulting in stable supply of biomass-derived rubber and attention to the environment according to the situation at the time of production. For example, biomass-derived butadiene can be prepared from the aforementioned various substrates such as bioethanol, biobutanol, and terpenes. Also, biomass-derived styrene can be prepared using various plants or microorganisms.

In cases where the biomass-derived monomer component is a combination of multiple types, the biomass-derived monomer component is preferably a combination of monomers derived from different biomass species, in other words, a combination of monomers obtained from different biomass resources. Specifically, it is preferred that the biomass-derived butadiene be a mixture of a plurality of biomass-derived butadienes of different origins, and/or that the biomass-derived styrene be a mixture of a plurality of biomass-derived styrenes of different origins. This allows effective use of a plurality of biomass resources and thus makes it possible to more suitably meet the aforementioned comprehensive environmental needs.

Another preferred method of converting the butadiene or styrene obtained from biomass resources to BSBR involves an enzymatic reaction. Some enzymes (long prenyl chain elongating enzymes) contained in rubber latex are known to have an effect of promoting the diene polymerization reaction. These enzymes can be used in the polymerization in vivo or in vitro.

The long prenyl chain elongating enzyme may be any conventionally known one.

BSBR may directly be prepared from biomass resources, for example, by a method of culturing (tissue culturing) at least one selected from the group consisting of microorganisms, plants, animals, and tissue cultures thereof, which are capable of diene polymerization, to directly convert a biomass resource to BSBR, or by a method of culturing at least one selected from the group consisting of microorganisms, plants, animals, and tissue cultures thereof in a medium containing butadiene (preferably obtained from biomass resources) and styrene (preferably obtained from biomass resources) to polymerize BSBR.

Suitable examples of the microorganisms or the like which are capable of diene polymerization include plants such as Hevea *brasiliensis, Ficus elastica, taraxacum, Ficus carica, Sonchus oleraceus, Solidago canadensis, Parthenium argentatum Gray, Manilkara zapota*, and *Eucommia ulmoides*, and tissue cultures thereof.

In culturing the microorganisms or the like, saccharides such as glucose are usually used as carbon source. Thus, all the compounds produced by the microorganisms or the like correspond to biomass resource-derived materials.

As described above, BSBR is polymerized from butadiene and styrene, provided that at least part of the butadiene starting material (butadiene monomer) and the styrene starting material (styrene monomer) is obtained by a reaction starting from biomass (a one-step reaction for preparing butadiene and/or styrene from biomass resources (reaction of directly generating butadiene and/or styrene from biomass resources)) or by a series of reactions starting from biomass (a series of reactions that generate butadiene and/or styrene using biomass resources as starting materials).

The biomass-derived rubber (preferably BSBR) content based on 100% by mass of the rubber component is preferably 20% by mass or more, and more preferably 30% by mass or more. Moreover, the upper limit of the content is not particularly limited, and is preferably 80% by mass or less, and more preferably 70% by mass or less. The use of the biomass-derived rubber (preferably BSBR) in the range mentioned above provides good fuel efficiency, wet grip performance, and processability (particularly, good wet grip performance and processability) while satisfying the requirements for a sound material-cycle society.

Examples of rubbers which can be used in the rubber component of the rubber compositions for tires, other than the biomass-derived rubber include natural rubber (NR), epoxidized natural rubber (ENR), diene synthetic rubber (polyisoprene rubber (IR), polybutadiene rubber (BR), styrene-butadiene rubber (SBR), styrene-isoprene-butadiene rubber (SIBR), chloroprene rubber (CR), acrylonitrile butadiene rubber (NBR), ethylene-propylene-diene rubber (EPDM), butyl rubber (IIR), and halogenated butyl rubber (X-IIR). These rubbers may be used alone or in combination of two or more. NR is preferred among these because its combined use with the biomass-derived rubber can provide good fuel efficiency, wet grip performance, processability, abrasion resistance, and flex fatigue resistance while satisfying the requirements for a sound material-cycle society.

The NR content based on 100% by mass of the rubber component is preferably 20% by mass or more, and more preferably 30% by mass or more. The NR content is also preferably 80% by mass or less, and more preferably 70% by mass or less. The use of NR in the range mentioned above can provide good fuel efficiency, wet grip performance, processability, abrasion resistance, and flex fatigue resistance while satisfying the requirements for a sound material-cycle society.

The rubber composition of the present invention preferably contains filler. The filler may be any conventionally known one for use in tires. Examples of the filler include silica, carbon black, aluminum hydroxide, clay, calcium carbonate, montmorillonite, cellulose, glass balloons, and various staple fibers. In view of tire physical properties, the filler is preferably silica, carbon black, or aluminum hydroxide. These fillers may be used alone or in combination of two or more.

The amount of filler per 100 parts by mass of the rubber component is preferably 10 to 200 parts by mass, more preferably 20 to 180 parts by mass, and still more preferably 30 to 150 parts by mass. An amount of less than 10 parts by mass tends to provide insufficient strength to the rubber composition, resulting in reduced abrasion resistance and reduced flex fatigue resistance. Conversely, if the amount is more than 200 parts by mass, the filler tends to insufficiently disperse in the rubber, resulting in a reduction in rubber physical properties (fuel efficiency, abrasion resistance, and flex fatigue resistance).

Silica is preferred among the fillers in view of improving fuel efficiency of the resulting tire.

The silica preferably has a nitrogen adsorption specific surface area ($N_2SA$) measured by the BET method of 50 $m^2/g$ or more, more preferably 100 $m^2/g$ or more. If the $N_2SA$ is less than 50 $m^2/g$, rubber strength tends to be reduced and abrasion resistance and flex fatigue resistance tend to be reduced. The $N_2SA$ is also preferably 250 $m^2/g$ or less, and more preferably 200 $m^2/g$ or less. If the $N_2SA$ is more than 250 $m^2/g$, processability tends to deteriorate and fuel efficiency, abrasion resistance, and flex fatigue resistance tend to deteriorate.

The $N_2SA$ of silica is determined by the BET method in accordance with ASTM D3037-93.

The amount of silica per 100 parts by mass of the rubber component is preferably 5 parts by mass or more, and more preferably 15 parts by mass or more. The amount of silica is preferably 200 parts by mass or less, more preferably 150 parts by mass or less, still more preferably 100 parts by mass or less, and particularly preferably 50 parts by mass or less. The use of silica in the range mentioned above can provide not only good fuel efficiency but also a good reinforcing effect (good abrasion resistance and flex fatigue resistance).

Carbon black is preferred among the fillers in view of improving the resulting tire in terms of grip performance, abrasion resistance, and flex fatigue resistance.

The nitrogen adsorption specific surface area ($N_2SA$) of carbon black is preferably 50 $m^2/g$ or more, and more preferably 90 $m^2/g$ or more. If the $N_2SA$ is less than 50 $m^2/g$, the reinforcibility may be insufficient, resulting in insufficient grip performance, abrasion resistance, and flex fatigue resistance. The $N_2SA$ is preferably 180 $m^2/g$ or less, and more preferably 130 $m^2/g$ or less. Carbon black with a $N_2SA$ exceeding 180 $m^2/g$ tends to be difficult to disperse, resulting in poor fuel efficiency, abrasion resistance, and flex fatigue resistance.

The $N_2SA$ of carbon black can be determined in conformity with JIS K 6217-2:2001.

The amount of carbon black per 100 parts by mass of the rubber component is preferably 5 parts by mass or more, and more preferably 15 parts by mass or more. An amount of less than 5 parts by mass may fail to give sufficient grip performance, abrasion resistance, and flex fatigue resistance. The amount of carbon black is preferably 100 parts by mass or less, more preferably 70 parts by mass or less, and still more preferably 50 parts by mass or less. An amount of more than 100 parts by mass tends to exhibit poor dispersibility and thus deteriorate fuel efficiency, abrasion resistance, and flex fatigue resistance.

In addition to the above components, the rubber compositions for tires may appropriately contain other compounding agents generally used in the preparation of rubber compositions, such as silane coupling agents, oil, stearic acid, zinc oxide, wax, antioxidants, vulcanizing agents, and vulcanization accelerators.

The rubber compositions of the present invention may be prepared by conventionally known methods. For example, the rubber compositions may be prepared by kneading the components using a rubber kneading device such as an open roll mill, a Banbury mixer, or an internal mixer, and then vulcanizing the mixture.

Moreover, after the ratio between the biomass-derived monomer component and the petroleum-derived monomer component is appropriately chosen depending on the comprehensive environmental needs at the time of the preparation of the rubber composition, including the biomass resource supply situation, the petroleum resource (e.g. petroleum-derived monomer component) supply situation, and/or market needs (e.g. the trend of competition with the demand for biomass resources as food), the biomass-derived monomer component or a combination of the biomass-derived monomer component and the petroleum-derived monomer component may be polymerized in the appropriately chosen ratio to form a biomass-derived rubber, whereby a biomass-derived rubber having the same level of performance as when conventional synthetic rubber is used can be prepared.

The tire components of the present invention may be prepared using the above rubber compositions by usual methods. Specifically, the unvulcanized rubber composition optionally combined with various additives may be extruded according to the shape of a tire component (e.g. tread, sidewall, bead filler, chafer, or clinch), formed, and heated and pressed in a vulcanizer to prepare a tire component.

The pneumatic tires of the present invention may be prepared using the above rubber compositions by usual methods. Specifically, the unvulcanized rubber composition optionally combined with various additives may be extruded according to the shape of a tire component such as a tread, formed on a tire building machine by a usual method and assembled with other tire components to build an unvulcanized tire, which may then be heated and pressed in a vulcanizer to form a tire.

The pneumatic tires of the present invention can be suitably used as tires for passenger cars, tires for trucks and buses, tires for two-wheeled vehicles, racing tires, and the like.

EXAMPLES

The present invention will be described in greater detail below by reference to, but not limited to, examples.

The butadienes, styrenes, and styrene-butadiene rubbers prepared in preparation examples mentioned later were evaluated by the methods below.

(pMC of Butadiene, Styrene, and Styrene-Butadiene Rubber)

The pMC of the butadienes, styrenes, and styrene-butadiene rubbers was measured by the following method in accordance with ASTM D 6866-10.

A sample (butadiene, styrene, or styrene-butadiene rubber) was burnt to generate carbon dioxide ($CO_2$), which was then purified through a vacuum line. Next, the purified carbon dioxide was reduced with hydrogen in the presence of an iron catalyst to generate graphite (C). Then, the obtained graphite was charged into a cathode (inner diameter: 1 mm) using a hand press. This cathode was put on a wheel and then mounted on a measurement system (a tandem accelerator-based system dedicated to $^{14}C$ AMS (NEC Corp.)). The measurement system measured $^{14}C$ content and $^{13}C$ content. Using oxalic acid from the National Bureau of Standards (National Institute of Standards and Technology (NIST)) as a standard sample, pMC (%) which indicates biomass content was calculated from the measured values. In the pMC calculation, the values were corrected with the $^{13}C$ content values.

(Styrene Content in Styrene-Butadiene Rubber)

Styrene content was measured using an NMR instrument AV400 and data analysis software TOP SPIN2.1 (both produced by BRUKER).

(Glass Transition Temperature (Tg) of Styrene-Butadiene Rubber)

Glass transition temperature (Tg) was measured using an automated differential scanning calorimeter (DSC-60A) produced by SHIMADZU CORPORATION at a temperature rise rate of 10° C./min according to JIS-K 7121.

(Weight Average Molecular Weight (Mw) and Molecular Weight Distribution (Mw/Mn) of Styrene-Butadiene Rubber)

Weight average molecular weight (Mw) and number average molecular weight (Mn) were measured by gel permeation chromatography (GPC) under the following conditions (1) to (8). Then the molecular weight distribution (Mw/Mn) of the polymer was calculated from the measured Mw and Mn values.

(1) Instrument: HLC-8020 produced by TOSOH CORPORATION
(2) Separation column: GMH-XL (2 columns in series) produced by TOSOH CORPORATION
(3) Measurement temperature: 40° C.
(4) Carrier: Tetrahydrofuran
(5) Flow rate: 0.6 mL/min
(6) Injection volume: 5 μL
(7) Detector: Differential refractometer
(8) Molecular weight standards: Polystyrene standards Preparation Example 1 (Preparation of Butadiene from Butanol)

<Preparation of Biobutanol>

A 300-ml fermenter (DASGIP) was filled with 250 ml of a synthetic medium (containing saccharides) of Soni et al. (Soni et al., Appl. Microbial. Biotechnol., 1987, vol. 27, pp. 1-5), and then sparged with nitrogen for 30 minutes. Then, *Clostridium acetobutylicum* (ATCC 824) was anaerobically inoculated in the medium. The culture temperature was maintained at constant 35° C., and the pH was adjusted to 5.5 using a $NH_4OH$ solution. During the culture, the anaerobic conditions were maintained and the shaking speed was maintained at 300 rpm. After five-day culture, the culture fluid was distilled and then separated by a conventionally well-known ion exchange resin technique, thereby providing biobutanol (1-butanol).

<Preparation of Butadiene from Biobutanol>

Using a system shown in FIG. 1, biomass-derived butadiene was synthesized from the biobutanol (1-butanol) prepared in <Preparation of biobutanol>.

The system used here (see FIG. 1) was provided with an alcohol feed pipe (material feed pipe) 21, a heater (electric furnace) 22 for vaporizing the fed alcohol, a dehydration column 23 for effecting dehydration reaction of the alcohol, a cooler 24 for cooling the product of the dehydration reaction and removing water from the purified alkene mixture, a heater 25 for vaporizing the alkene, a second reaction column 26 for further effecting dehydrogenation reaction of the alkene to synthesize butadiene, and a cooler 27 for collecting the generated reaction product. The dehydration column 23 was packed with 10 g of aluminum oxide (101095100, Merck) as catalyst.

A catalyst for the second dehydrogenation reaction was prepared as follows. Chromium nitrate (5.8 g) was dissolved in ion-exchange water. Then, SSZ-35 zeolite (6 g, silica/alumina ratio: 40) was put into and impregnated with the solution and left to stand overnight. Subsequently, the product was dried in a 100° C. oven to give a precursor. This precursor was put in a ceramic container and then fired for three hours at 700° C. in the air, thereby providing a chromium-supported zeolite catalyst containing 10% by mass of chromium.

Then, the second reaction column 26 was packed with 10 g of the chromium-supported zeolite catalyst.

Nitrogen gas was supplied to the dehydration column 23 through a gas feed pipe (not shown). The nitrogen gas was supplied at a LHSV rate of 1/hr. After the dehydration column 23 was heated to a predetermined temperature with the heater 22, a predetermined amount of the biobutanol was supplied through the alcohol feed pipe 21. The reaction conditions were as follows: reaction temperature was 500° C., reaction pressure was atmospheric pressure, and molar ratio of biobutanol to nitrogen was 50/50 (biobutanol/nitrogen). The reaction time was two hours. The resulting product was collected in the cooler (product trap) 24 connected to the dehydration column 23, and water was then separated away.

The second reaction column 26 was heated to 500° C. The cooler (product trap) 27 was cooled down to −20° C. A pre-heated gas mixture ((the butene mixture obtained in the first dehydration reaction)/(nitrogen)/(air)=1:1:1) was fed at a LHSV supply rate of 1/hr through the cooler (product trap) 24. The resulting reaction mixture was separated and purified by the method disclosed in JP S60-115532 A to give biomass-derived butadiene at a yield of 8%. The pMC (which indicates biomass content) of the obtained butadiene (biomass-derived butadiene) was 105%.

Preparation Example 2 (Preparation of Butadiene from Bioethanol)

Using the system shown in FIG. 1, biomass-derived butadiene was synthesized from a commercially available bioethanol by a conventionally known method of converting ethanol to butadiene (Kirshenbaum, I., "Butadiene", Encyclopedia of Chemical Technology, 3rd ed., vol. 4, Grayson, M., (ed.), John Wiley & Sons, New York, 1978, pp. 313-337). The pMC (which indicates biomass content) of the obtained butadiene (biomass-derived butadiene) was 108%.

Preparation Example 3 (Preparation of Butadiene from Bioethylene)

A catalyst prepared by dissolving palladium acetate (0.5 mmol/L) in $Na_3H_3PMo_9V_3O_{40}$ (0.3 mol/L) was introduced into the second reaction column 26 of the system shown in FIG. 1, and the system was purged with argon. Then a biomass-derived ethylene (trial product formed from corn-derived bioethanol) was fed into the system. A reaction was allowed to proceed for one hour while the catalyst solution was circulated in the system through a circulation line 28 at 150° C. and 0.5 MpaG. After the catalyst solution was removed through a drain of the cooler 27, an alumina catalyst (alumina KHA-46 from Sumitomo Chemical Co., Ltd.) immersed in bioethanol was put therein and a reaction was allowed to proceed at 400° C. for five hours. The reaction mixture was analyzed by GC/MS to confirm the formation of butadiene. The pMC (which indicates biomass content) of the obtained butadiene (biomass-derived butadiene) was 109%.

Preparation Example 4 (Preparation of Butadiene from Tiglic Acid)

An argon-filled autoclave was charged with 500 mg of tiglic acid (an intermediate of an amino acid-mediated in-vivo reaction) separated and purified from croton oil, 30 mg of tetrakis(triphenylphosphine)palladium(0), and 10 mg of triethylboron, and the contents were reacted at 200° C. for one hour. The resulting product was analyzed by GC/MS to confirm the formation of butadiene. The pMC (which indicates biomass content) of the obtained butadiene (biomass-derived butadiene) was 108%.

The biomass-derived butadienes prepared in Preparation Examples 1 to 4 were analyzed using an NMR instrument AV400 (with data analysis software TOP SPIN 2.1) from BRUKER to confirm these butadienes to be 1,3-butadiene.

Preparation Example 5 (Preparation of Styrene from Trees of the Family Hamamelidaceae)

Part of bark was peeled off trees of *Liquidambar styraciflua*, and a resin exuded therefrom was collected. The collected resin (620 g in total) was immersed in toluene, and left to stand for half a day. Then, the toluene solution was filtered and distilled to obtain a fraction (2.4 g) boiling between 130 and 160° C. The obtained fraction was purified by HPLC to separate 0.8 g of styrene. The pMC (which indicates biomass content) of the obtained styrene (biomass-derived styrene) was 109%.

Separately, 1 kg of the peeled bark was treated in the same manner as above to give 0.8 g of styrene. The pMC (which indicates biomass content) of the obtained styrene (biomass-derived styrene) was 109%.

Preparation Example 6 (Preparation of Styrene from Trees of the Family Styracaceae)

A resin (610 g) of trees of *Styrax japonica* was treated in the same manner as in Preparation Example 5 to give styrene (0.1 g). The pMC (which indicates biomass content) of the obtained styrene (biomass-derived styrene) was 109%.

Preparation Example 7 (Preparation of Styrene by Plant Tissue Culture)

Buds were cut from *Catharanthus roseus* and immersed in a 70% ethanol solution and then in an approximately 0.5% sodium hypochlorite solution, followed by washing with sterile water. The washed tissue section (bud) was placed on an MS medium supplemented with 1.0 mg/l of dichlorophenoxyacetic acid and 1.0 mg/l of benzyl adenine. The tissue section was cultured at 25° C. for five weeks to form a callus.

Next, the callus (10 g) was transplanted in 20 ml of a Gamborg B5 liquid medium (Gamborg O. L., Miller R. A., Ojima K., Experimental Cell Research, 50, pp. 151-158 (1968).) supplemented with 50 mg of biomass-derived cinnamic acid, 1.0 mg/l of dichlorophenoxyacetic acid, 1.0 mg/l of benzyl adenine, and 3% of sucrose. The callus was cultured for 12 days at a culture temperature of 25° C. in a dark atmosphere while shaking at a rotation rate of 100 rpm.

The tissue culture was taken out and washed with water, dried, and freeze ground. The freeze ground tissue was extracted with hexane, and the extract was purified by HPLC to separate 6 mg of styrene. The pMC (which indicates biomass content) of the obtained styrene (biomass-derived styrene) was 109%.

The biomass-derived cinnamic acid was prepared by further purifying cinnamic acid derived from herbs (*Scrophulariaceae Juss.*) sold for aromatherapy use by high-performance liquid chromatography.

Preparation Example 8 (Preparation of Styrene with Non-Genetically Modified Microorganism)

Potato dextrose medium powder (produced by Sigma-Aldrich) (24 g) was dissolved in purified water (1000 mL), followed by sterilization in an autoclave at 121° C. for 20 minutes. Chloramphenicol was added to a final concentration of 100 mg/L before use.

*Penicillium citrinum* (ATCC 9849) was inoculated in the medium and statically cultured under sealed conditions at 25° C. for two weeks. Then, hexane was added to the culture container and shaken. Subsequently, the hexane layer was separated and analyzed by GC/MS to confirm the formation of styrene. The pMC (which indicates biomass content) of the obtained styrene (biomass-derived styrene) was 109%.

Preparation Example 9 (Preparation of Styrene with Genetically Modified *Escherichia coli*)

<Preparation of encP Gene (Phenylalanine Ammonia-Lyase Encoding Gene) Fragment and Construction of encP Expression Plasmid>

A *Streptomyces maritimus* (*actinomyces* bacterium) encP gene (1572 bp from the initiation codon to the stop codon (GenBank accession number: AF254925, nucleotide number 16269 to 17840)) was prepared as artificial gene, and a DNA in which the gene was inserted into a SmaI site in the cloning vector pUC19 plasmid was used as a template for PCR. PCR was performed using an upstream primer (SEQ ID No: 1) containing a NdeI site at the 5' end and a downstream primer (SEQ ID No: 2) containing a BamHI site at the 5' end. The reaction solution was purified using QIA prep PCR Purification Kit (produced by QIAGEN) to give a DNA fragment E (NdeI-encP-BamHI: 1592 bp) consisting of the encP gene containing new restriction enzyme sites at both ends.

According to general recombinant DNA techniques, the DNA fragment E treated with a NdeI restriction enzyme and a BamHI restriction enzyme was ligated into the NdeI/BamHI site of a pET11a vector (Novagen), and transfected into *Escherichia coli* DH-5α competent cells, and the cells were inoculated in an LB agar medium containing ampicillin (50 µg/mL), followed by culture overnight at 37° C. *Escherichia coli* colonies formed in the agar medium were cultured in an LB liquid medium (5 mL) containing ampicillin (50 µg/mL) with shaking at 37° C. for one night. The plasmid was extracted from the obtained *Escherichia coli* cells using QIAprep Spin Miniprep Kit (QIAGEN). DNA sequence analysis of the plasmid confirmed that the DNA sequence of GenBank accession number AF254925 was inserted into the target site of the pET11a vector. This plasmid was taken as encP expression plasmid pET11-encP (plasmid illustrated in FIG. 2(*a*)).

<Isolation of FDC1 Gene (Ferulic Acid Decarboxylase Encoding Gene)>

Genomic DNA was purified from the budding yeast *Saccharomyces cerevisiae* using Yeast Geno-DNA-Template (Geno Technology, Inc.) and used as a template for the first PCR. The PCR was performed using an upstream primer (SEQ ID No: 3) and a downstream primer (SEQ ID No: 4), the reaction solution was purified using QIAprep PCR purification Kit (QIAGEN), and the resulting DNA was used as a template for the second PCR. The second PCR was performed using an upstream primer (SEQ ID No: 5) containing a BspHI site at the 5' end and a downstream primer (SEQ ID No: 6) containing a HindIII site at the 5' end, and the reaction solution was purified using QIAprep PCR purification Kit (QIAGEN) to give a DNA fragment F (BspHI-FDC1-HindIII: 1525 bp) consisting of the FDC1 gene with new restriction enzyme sites added to both ends.

<Isolation of PAD1 Gene (Cinnamate Decarboxylase (Phenylacrylate Decarboxylase) Encoding Gene)>

PCR was performed using the above-described *Saccharomyces cerevisiae* genome as a template with an upstream primer (SEQ ID No: 7) and a downstream primer (SEQ ID No: 8). The reaction solution was purified using PCR purification Kit (QIAGEN), and the resulting DNA was used as a template for the second PCR. The second PCR was performed using an upstream primer (SEQ ID No: 9) containing a NdeI site at the 5' end and a downstream primer (SEQ ID No: 10) containing a XhoI site at the 5' end, and the reaction solution was purified using QIAprep PCR purification Kit (QIAGEN) to give a DNA fragment P (NdeI-PAD1-XhoI: 746 bp) consisting of the PAD1 gene with new restriction enzyme sites added to both ends.

<Construction of FDC1/PAD1 Coexpression Plasmid>

The FDC1 gene DNA fragment F and the PAD1 gene DNA fragment P were inserted into the multiple cloning site-1 (MCS-1) and the multiple cloning site-2 (MCS-2) of pRSFDuet-1 (Novagen), respectively, in the following ways.

According to general recombinant DNA techniques, the DNA fragment F treated with a BspHI restriction enzyme and a HindIII restriction enzyme was inserted between the NcoI site and the HindIII site in the multiple cloning site-1 of the pRSFDuet-1 vector (Novagen). pRSF-FDC1 was constructed in the same way as for the construction of pET11-encP, except that kanamycin was used instead of ampicillin in the agar medium and the liquid medium.

Figure 2:
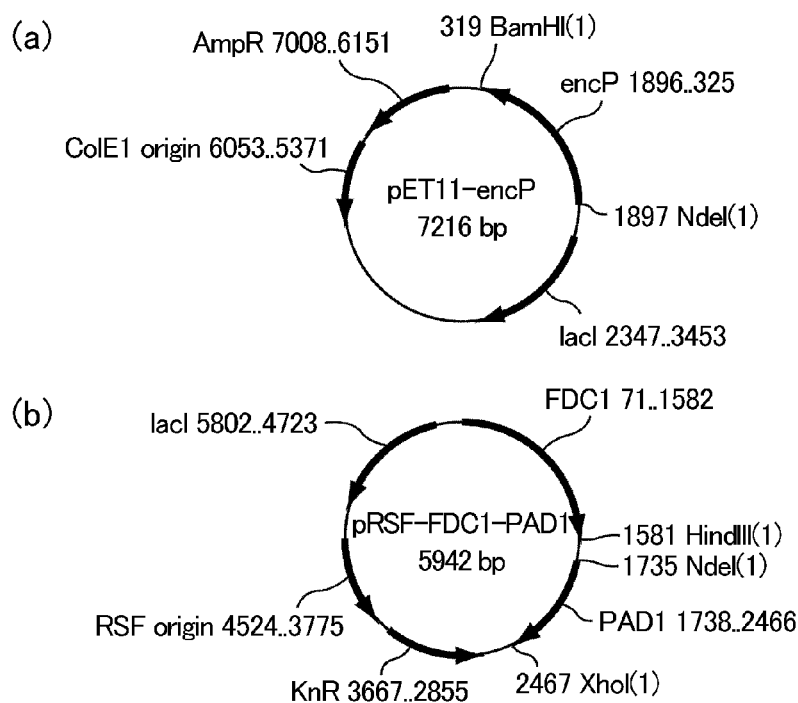
FIG. 2 shows views schematically illustrating prepared plasmids.

Similarly, the DNA fragment P treated with a NdeI restriction enzyme and a XhoI restriction enzyme was incorporated between the NdeI site and the XhoI site (derived from MCS-2 of the original vector pRSFDuet-1) of pRSF-FDC1 to construct a plasmid which was taken as pRSF-FDC1-PAD1 (plasmid illustrated in FIG. 2(*b*)).

<Preparation of Transformant> pET11-encP and pRSF-FDC1-PAD1 were simultaneously transfected into *Escherichia coli* BL21 (DE3) competent cells, and the cells were inoculated in an LB agar medium containing ampicillin (35 µg/mL) and kanamycin (20 µg/mL), and then cultured overnight at 30° C. The formation of *Escherichia coli* colonies in the agar medium was observed.

<Production of Styrene by Transformant>

The *Escherichia coli* colonies transfected with pET11-encP and pRSF-FDC1-PAD1 were inoculated in an LB liquid medium (1 mL) containing ampicillin (35 µg/mL) and kanamycin (20 µg/mL), and then cultured with shaking overnight at 30° C. to prepare a preculture fluid. The preculture fluid (100 µL) was inoculated in an LB liquid medium (50 mL) containing ampicillin (35 µg/mL) and kanamycin (20 µg/mL) in a 300-mL erlenmeyer flask, and then cultured with shaking at 30° C. for 15 hours. The culture was further continued under the same conditions while the absorbance (A600) of the culture fluid was measured at a wavelength of 600 nm every 30 minutes. When the A600 reached 0.8, 1M isopropyl-β-thiogalactopyranoside (IPTG) (25 µL, final concentration 0.5 mM) was added in order to induce protein expression, and the culture was further performed for eight hours.

<Measurement of Amount of Styrene Produced in Culture Fluid>

The culture fluid was centrifuged to separate a supernatant. Hexane was added to the supernatant and they were vigorously stirred. After centrifugation, the hexane layer was separated and analyzed by GC/MS to confirm the formation of styrene. The amount of styrene produced was 140 mg/L. The pMC (which indicates biomass content) of the obtained styrene (biomass-derived styrene) was 109%.

Preparation Example 10 (Preparation of Biomass Styrene-Butadiene Rubber (BSBR))

BSBR (corresponding to a biomass-derived rubber of the present invention) was synthesized using, as the monomer component, a mixture of the biomass-derived butadienes (1,3-butadienes) obtained in Preparation Examples 1 to 4 as biomass-derived butadiene, and a mixture of the biomass-derived styrenes obtained in Preparation Examples 5 to 9 as biomass-derived styrene.

The chemicals used are listed below.
Cyclohexane: Anhydrous cyclohexane produced by KANTO CHEMICAL CO., INC.
Butadiene: Mixture of biomass-derived butadienes obtained in Preparation Examples 1 to 4
Styrene: Mixture of biomass-derived styrenes obtained in Preparation Examples 5 to 9
TMEDA: Tetramethylethylenediamine produced by KANTO CHEMICAL CO., INC.

Butyllithium solution: 1.6 M-n-butyllithium/hexane solution produced by KANTO CHEMICAL CO., INC.
BHT solution: Solution prepared by dissolving 0.1 g of BHT (2,6-tert-butyl-p-cresol) (produced by KANTO CHEMICAL CO., INC.) in 100 ml of isopropanol (produced by KANTO CHEMICAL CO., INC.)

<Synthesis of BSBR>

A reactor (500-ml pressure-resistant stainless-steel vessel) was purged with nitrogen. While maintaining a nitrogen atmosphere, the reactor was charged with cyclohexane (180 ml), butadiene (20 ml, 222 mmol), styrene (3.5 ml, 30 mmol), and TMEDA (0.3 ml, 2 mmol) and then stirring was started.

Next, the inside of the vessel was heated to 40° C., and a butyllithium solution (0.06 ml) was added to initiate polymerization. After 3 hours of stirring, a BHT solution (0.1 ml) was added to the polymer solution, and the solution was then stirred for five minutes. Subsequently, the polymer solution was taken out, and poured into ethanol (300 ml) with stirring so that the polymerized product was coagulated. The obtained polymerized product was dried by air, and then dried under reduced pressure for 24 hours. Thus, a biomass styrene-butadiene rubber (BSBR) was obtained with a yield of 95%. As a result of analysis of the BSBR, Mw was $40.2 \times 10^4$, Mw/Mn was 1.07, pMC (which indicates biomass content) was 108%, Tg was −25° C., and styrene content was 22.3% by mass.

The chemicals used in the example and comparative examples are listed below.
NR: RSS#3 (Tg: −75° C.)
SBR: NS116 (Tg: −25° C., styrene content: 21% by mass, Mw: $68.7 \times 10^4$, Mw/Mn: 1.12) produced by ZEON CORPORATION
BSBR: Biomass styrene-butadiene rubber obtained in Preparation Example 10 (corresponding to a biomass-derived rubber of the present invention)
Carbon black: SEAST N220 ($N_2SA$: 114 $m^2/g$) produced by Mitsubishi Chemical Corporation
Silica: ULTRASIL VN3 (average primary particle size: 15 nm, $N_2SA$: 175 $m^2/g$) produced by Evonik Degussa
Silane coupling agent: Si75 (bis(3-triethoxysilylpropyl)disulfide) produced by Evonik Degussa
Oil: Process X-140 produced by JX Nippon Oil & Energy Corporation
Wax: SUNNOC N produced by OUCHI SHINKO CHEMICAL INDUSTRIAL CO., LTD.
Zinc oxide: Zinc oxide #1 produced by Mitsui Mining and Smelting Co., Ltd.
Stearic acid: Stearic acid "TSUBAKI" produced by NOF CORPORATION
Antioxidant: Antigene 6C (N-(1,3-dimethylbutyl)-N'-phenyl-p-phenylenediamine) produced by Sumitomo Chemical Co., Ltd.
Sulfur: Powder sulfur produced by Karuizawa Iou K.K.
Vulcanization accelerator 1: Nocceler CZ (N-cyclohexyl-2-benzothiazolylsulfenamide) produced by Ouchi Shinko Chemical Industrial Co., Ltd.
Vulcanization accelerator 2: Nocceler D (N,N'-diphenylguanidine) produced by Ouchi Shinko Chemical Industrial Co., Ltd.

Example and Comparative Examples

The chemicals except the sulfur and vulcanization accelerators were kneaded with a 1.7-L Banbury mixer in accordance with each of the formulations shown in Table 1. Then the kneaded mixture was combined with the sulfur and vulcanization accelerators and they were kneaded with an open roll mill to prepare an unvulcanized rubber composition. The obtained unvulcanized rubber composition was then press-vulcanized using a 2 mm-thick mold at 170° C. for 15 minutes to prepare a vulcanized rubber composition (vulcanized rubber sheet).

The thus prepared unvulcanized rubber compositions and vulcanized rubber compositions were evaluated for the following items. The results are shown in Table 1.

(1) Rolling Resistance Index

The tan δ of each formulation (vulcanized rubber composition) was measured using a viscoelasticity spectrometer VES (produced by Iwamoto Seisakusho Co., Ltd.) at 70° C., an initial strain of 10%, and a dynamic strain of 2%. The measured values are expressed as an index calculated using the following equation, with the tan δ value of Comparative Example 1 being set equal to 100. A higher index indicates better rolling resistance properties (better fuel efficiency).

(Rolling resistance index)=(tan δ of Comparative Example 1)/(tan δ of each formulation)×100

(2) Wet Performance Index

The tan δ of each formulation (vulcanized rubber composition) was measured using a viscoelasticity spectrometer VES (produced by Iwamoto Seisakusho Co., Ltd.) at 20° C., an initial strain of 10%, and a dynamic strain of 2%. The measured values are expressed as an index calculated using the following equation, with the tan δ value of Comparative Example 1 being set equal to 100. A higher index indicates better wet performance (better wet grip performance).

(Wet performance index)=(tan δ of each formulation)/(tan δ of Comparative Example 1)×100

(3) Processability Index

The Mooney viscosity ($ML_{1+4}/130°$ C.) of each unvulcanized rubber composition was determined using a Mooney viscosity tester in accordance with JIS K6300-1 "Rubber, unvulcanized—Physical property—Part 1: Determination of Mooney viscosity and pre-vulcanization characteristics with Mooney viscometer," as follows: The Mooney viscosity tester was preheated for one minute to 130° C., and a small rotor was rotated at this temperature. After four minutes of rotation, Mooney viscosity ($ML_{1+4}/130°$ C.) was measured. The Mooney viscosities of the formulations are expressed as an index calculated using the following equation, with the value of Comparative Example 1 being set equal to 100. A higher index indicates a lower Mooney viscosity and therefore better processability.

(Processability index)=(Mooney viscosity of Comparative Example 1)/(Mooney viscosity of each formulation)×100

TABLE 1

|  |  | Example 1 | Comparative Example 1 | Comparative Example 2 |
|---|---|---|---|---|
| Amount (parts by mass) | NR | 50 | 100 | 50 |
|  | SBR | — | — | 50 |
|  | BSBR | 50 | — | — |
|  | Carbon black | 30 | 30 | 30 |
|  | Silica | 30 | 30 | 30 |
|  | Silane coupling agent | 3 | 3 | 3 |
|  | Oil | 20 | 20 | 20 |
|  | Wax | 2 | 2 | 2 |
|  | Zinc oxide | 2 | 2 | 2 |
|  | Stearic acid | 2 | 2 | 2 |

TABLE 1-continued

|  |  | Example 1 | Comparative Example 1 | Comparative Example 2 |
|---|---|---|---|---|
|  | Antioxidant | 2 | 2 | 2 |
|  | Sulfur | 2 | 2 | 2 |
|  | Vulcanization accelerator (1) | 1 | 1 | 1 |
|  | Vulcanization accelerator (2) | 1.5 | 1.5 | 1.5 |
| Evaluation result | pMC | 105 | 105 | 53 |
|  | Rolling resistance index | 105 | 100 | 105 |
|  | Wet performance index | 130 | 100 | 130 |
|  | Processability index | 120 | 100 | 120 |

Table 1 shows that in Comparative Example 2 using 50% by mass of NR and 50% by mass of SBR in the rubber component, good fuel efficiency, wet grip performance, and processability were exhibited, but the pMC of the total rubber component was low and thus this comparative example could not sufficiently satisfy the requirements for a sound material-cycle society. In Comparative Example 1 using 100% by mass of NR in the rubber component, the pMC of the total rubber component was high and thus this comparative example could satisfy the requirements for a sound material-cycle society, but fuel efficiency, wet grip performance, and processability (particularly, wet grip performance and processability) were greatly reduced. In contrast, in Example 1 using 50% by mass of NR and 50% by mass of BSBR in the rubber component, the pMC of the total rubber component was high and thus this example could satisfy the requirements for a sound material-cycle society, and, at the same time, good fuel efficiency, wet grip performance, and processability (particularly, good wet grip performance and processability) were exhibited.

REFERENCE SIGNS LIST

21 Alcohol feed pipe (material feed pipe)
22 Heater (electric furnace)
23 Dehydration column
24 Cooler
25 Heater
26 Second reaction column
27 Cooler
28 Circulation line

SEQUENCE LISTING FREE TEXT

SEQ ID No: 1: Upstream primer (encP-U-Nde)
SEQ ID No: 2: Downstream primer (encP-L-Bam)
SEQ ID No: 3: Upstream primer (FDC1-gU)
SEQ ID No: 4: Downstream primer (FDC1-gL)
SEQ ID No. 5: Upstream primer (FDC1-nU-BspHI)
SEQ ID No. 6: Downstream primer (FDC1-nL-Hind)
SEQ ID No. 7: Upstream primer (PAD1-gU)
SEQ ID No. 8: Downstream primer (PAD1-gL)
SEQ ID No. 9: Upstream primer (PAD1-nU-Nde)
SEQ ID No. 10: Downstream primer (PAD1-nL-Xho)

The invention claimed is:

1. A method of producing a rubber composition for tires, the method comprising:
   a step (A) of preparing butadiene by a catalytic reaction from at least one biomass-derived ingredient selected from the group consisting of biomass-derived ethylene, and unsaturated carboxylic acids;
   a step (B) of preparing styrene using at least one selected from the group consisting of microorganisms, plants, and tissue cultures thereof; and
   a step (C) of polymerizing the butadiene prepared in the step (A) and the styrene prepared in the step (B) to prepare a biomass-derived styrene-butadiene rubber having a pMC (percent modern carbon) measured in accordance with ASTM D 6866-10 of 1% or higher,
   wherein, when the step (A) is a step of preparing butadiene by catalysis from ethylene, the step (A) comprises:
       partially converting ethylene into acetaldehyde using an oxidation catalyst, and
       forming butadiene by subjecting the acetaldehyde to a dehydration reaction with the remaining ethylene using a dehydration catalyst.

2. The method of producing a rubber composition for tires according to claim 1,
   wherein the biomass-derived styrene-butadiene rubber has a glass transition temperature (Tg) of −60° C. or higher.

3. The method of producing a rubber composition for tires according to claim 1,
   wherein the at least one of the unsaturated carboxylic acids is at least one of tiglic acid and angelic acid.

4. The method of producing a rubber composition for tires according to claim 1,
   wherein the styrene is converted from biomass-derived cinnamic acid.

5. The method of producing a rubber composition for tires according to claim 1,
   wherein the at least one of the plants is at least one selected from the group consisting of plants of the families Hamamelidaceae, Styracaceae, Apocynaceae, Solanaceae, Daucus, and Theaceae.

6. The method of producing a rubber composition for tires according to claim 1,
   wherein the at least one of the microorganisms is at least one selected from the group consisting of microorganisms of the genera *Fusarium, Penicillium, Pichia, Candida, Debaryomyces, Torulopsis, Saccharomyces, Bacillus, Escherichia, Streptomyces*, and *Pseudomonas*.

7. The method of producing a rubber composition for tires according to claim 1,
   wherein the at least one of the microorganisms is not genetically modified.

8. The method of producing a rubber composition for tires according to claim 1,
   wherein the at least one of the microorganisms and plants is engineered so as to highly express phenylalanine ammonia-lyase.

9. The method of producing a rubber composition for tires according to claim 1,
   wherein the at least one of the microorganisms and plants is engineered so as to highly express cinnamate decarboxylase (phenylacrylate decarboxylase).

10. The method of producing a rubber composition for tires according to claim 1,
    wherein the at least one of the microorganisms and plants is engineered so as to highly express phenolic acid decarboxylase.

11. The method of producing a rubber composition for tires according to claim 1,
    wherein the styrene is obtained from biomass-derived cinnamic acid by plant metabolism.

12. The method of producing a rubber composition for tires according to claim 1,
    wherein the styrene is obtained from biomass-derived cinnamic acid by microbial fermentation.

13. The method of producing a rubber composition for tires according to claim 1,
    wherein the step (C) comprises polymerizing a plurality of butadienes of different origins.

14. The method of producing a rubber composition for tires according to claim 1,
    wherein the step (C) comprises polymerizing a plurality of styrenes of different origins.

15. The method of producing a rubber composition for tires according to claim 1,
    wherein the biomass-derived styrene-butadiene rubber has a pMC of 100% or higher.

16. A method of producing a tire component, the method comprising:
    a step (A) of preparing butadiene by a catalytic reaction from at least one biomass-derived ingredient selected from the group consisting of biomass-derived ethylene, and unsaturated carboxylic acids;
    a step (B) of preparing styrene using at least one selected from the group consisting of microorganisms, plants, and tissue cultures thereof; and
    a step (C) of polymerizing the butadiene prepared in the step (A) and the styrene prepared in the step (B) to prepare a biomass-derived styrene-butadiene rubber having a pMC (percent modern carbon) measured in accordance with ASTM D 6866-10 of 1% or higher,
    wherein, when the step (A) is a step of preparing butadiene by catalysis from ethylene, the step (A) comprises:
        partially converting ethylene into acetaldehyde using an oxidation catalyst, and
        forming butadiene by subjecting the acetaldehyde to a dehydration reaction with the remaining ethylene using a dehydration catalyst.

17. A method of producing a pneumatic tire, the method comprising:
    a step (A) of preparing butadiene by a catalytic reaction from at least one biomass-derived ingredient selected from the group consisting of biomass-derived ethylene, and unsaturated carboxylic acids;
    a step (B) of preparing styrene using at least one selected from the group consisting of microorganisms, plants, and tissue cultures thereof; and
    a step (C) of polymerizing the butadiene prepared in the step (A) and the styrene prepared in the step (B) to prepare a biomass-derived styrene-butadiene rubber having a pMC (percent modern carbon) measured in accordance with ASTM D 6866-10 of 1% or higher,
    wherein, when the step (A) is a step of preparing butadiene by catalysis from ethylene, the step (A) comprises:
        partially converting ethylene into acetaldehyde using an oxidation catalyst, and
        forming butadiene by subjecting the acetaldehyde to a dehydration reaction with the remaining ethylene using a dehydration catalyst.

18. The method of producing a rubber composition for tires according to claim 2, wherein the at least one of the unsaturated carboxylic acids is at least one of tiglic acid and angelic acid.

* * * * *

```
                        SEQUENCE LISTING

<160> NUMBER OF SEQ ID NOS: 10

<210> SEQ ID NO 1
<211> LENGTH: 36
<212> TYPE: DNA
<213> ORGANISM: Artificial Sequence
<220> FEATURE:
<223> OTHER INFORMATION: Downstream primer (encP-U-Nde)

<400> SEQUENCE: 1
cgtacatatg atgaccttcg tcatagagct cgacat                           36

<210> SEQ ID NO 2
<211> LENGTH: 26
<212> TYPE: DNA
<213> ORGANISM: Artificial Sequence
<220> FEATURE:
<223> OTHER INFORMATION: Upstream primer (encP-L-Bam)

<400> SEQUENCE: 2
tattggatcc tcagtgcgcc gccacg                                      26

<210> SEQ ID NO 3
<211> LENGTH: 21
<212> TYPE: DNA
<213> ORGANISM: Artificial Sequence
<220> FEATURE:
<223> OTHER INFORMATION: Downstream primer (FDC1-gU)

<400> SEQUENCE: 3
tcacgaaagt ccaaattgcg t                                           21

<210> SEQ ID NO 4
<211> LENGTH: 21
```

```
<212> TYPE: DNA
<213> ORGANISM: Artificial Sequence
<220> FEATURE:
<223> OTHER INFORMATION: Upstream primer (FDC1-gL)

<400> SEQUENCE: 4
gttaatggcg cactgcttgt c                                          21

<210> SEQ ID NO 5
<211> LENGTH: 33
<212> TYPE: DNA
<213> ORGANISM: Artificial Sequence
<220> FEATURE:
<223> OTHER INFORMATION: Downstream primer (FDC1-nU-BspHI)

<400> SEQUENCE: 5
cgactcatga ggaagctaaa tccagcttta gaa                             33

<210> SEQ ID NO 6
<211> LENGTH: 45
<212> TYPE: DNA
<213> ORGANISM: Artificial Sequence
<220> FEATURE:
<223> OTHER INFORMATION: Upstream primer (FDC1-nL-Hind)

<400> SEQUENCE: 6
gccaagctta tttatatccg tacctttttcc aattttcatt tactt               45

<210> SEQ ID NO 7
<211> LENGTH: 20
<212> TYPE: DNA
<213> ORGANISM: Artificial Sequence
<220> FEATURE:
<223> OTHER INFORMATION: Downstream primer (PAD1-gU)

<400> SEQUENCE: 7
gcattcctgt ctgaaagcct                                            20

<210> SEQ ID NO 8
<211> LENGTH: 21
<212> TYPE: DNA
<213> ORGANISM: Artificial Sequence
<220> FEATURE:
<223> OTHER INFORMATION: Upstream primer (PAD1-gL)

<400> SEQUENCE: 8
tgatatcggg aagttcacgg t                                          21

<210> SEQ ID NO 9
<211> LENGTH: 39
<212> TYPE: DNA
<213> ORGANISM: Artificial Sequence
<220> FEATURE:
<223> OTHER INFORMATION: Downstream primer (PAD1-nU-Nde)

<400> SEQUENCE: 9
cgtccatatg ctcctatttc caagaagaac taatatagc                       39

<210> SEQ ID NO 10
<211> LENGTH: 36
<212> TYPE: DNA
<213> ORGANISM: Artificial Sequence
<220> FEATURE:
<223> OTHER INFORMATION: Upstream primer (PAD1-nL|Xho)

<400> SEQUENCE: 10
cagtctcgag ttacttgctt tttattcctt cccaac                          36
```